(12) United States Patent
Li

(10) Patent No.: US 7,737,300 B2
(45) Date of Patent: Jun. 15, 2010

(54) PROCESSES AND INTERMEDIATES PREPARING CYSTEINE PROTEASE INHIBITORS

(75) Inventor: Jiayao Li, Foster City, CA (US)

(73) Assignee: ViroBay, Inc., Menlo Park, CA (US)

( * ) Notice: Subject to any disclaimer, the term of this patent is extended or adjusted under 35 U.S.C. 154(b) by 556 days.

(21) Appl. No.: 11/662,933

(22) PCT Filed: Sep. 16, 2005

(86) PCT No.: PCT/US2005/033051

§ 371 (c)(1),
(2), (4) Date: Mar. 16, 2007

(87) PCT Pub. No.: WO2006/034004

PCT Pub. Date: Mar. 30, 2006

(65) Prior Publication Data

US 2008/0114175 A1    May 15, 2008

(51) Int. Cl.
*C07C 231/12* (2006.01)
(52) U.S. Cl. ..................... 564/124
(58) Field of Classification Search ................... 564/124
See application file for complete search history.

(56) References Cited

FOREIGN PATENT DOCUMENTS

| WO | WO 00/49007 | * | 9/2000 |
| WO | WO 03/029200 | * | 4/2003 |
| WO | WO 03/075836 | * | 9/2003 |

OTHER PUBLICATIONS

Cited in the ISR of pct/us05/033051.*

* cited by examiner

*Primary Examiner*—Taofiq A Solola
(74) *Attorney, Agent, or Firm*—Townsend and Townsend and Crew LLP

(57) ABSTRACT

The present invention is directed to a process for preparing certain cysteine protease inhibitors.

1 Claim, No Drawings

PROCESSES AND INTERMEDIATES PREPARING CYSTEINE PROTEASE INHIBITORS

BACKGROUND OF THE INVENTION

1. Field of the Invention

The present invention is directed to a novel processes for preparing certain cysteine protease inhibitors.

2. State of the Art

WO 03/075836 and Applicant's provisional application Ser. No. 60/504,680 filed on Sep. 18, 2003, disclose certain cysteine protease inhibitors that are useful in the treatment of diseases such as osteoporosis, certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis, allergic disorders, including, but not limited to asthma; and allogeneic immune responses, including, but not limited to, rejection of organ transplants or tissue grafts.

The processes disclosed to prepare the compounds in these applications are unattractive for large scale synthesis of these compounds since they are lengthy and/or involve harsh reaction conditions which are unsuitable for a wide variety of substitutents. Accordingly, there is a need for synthetic processes that are facile and/or utilize reaction conditions that are amenable to a variety of substituents and therefore attractive on commercial scale. The present invention fulfills this and related needs.

SUMMARY OF THE INVENTION

In a first aspect, this invention is directed to a process of preparing a compound of Formula (I):

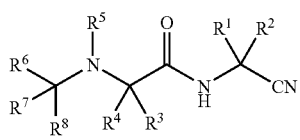

(I)

wherein:

$R^1$ is hydrogen or alkyl;

$R^2$ is hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, or -alkylene-X—$R^9$ (where X is —O—, —$NR^{10}$—, —$CONR^{11}$—, —$S(O)_{n1}$—, —$NR^{12}CO$—, —CO—, or —C(O)O— where n1 is 0-2, and $R^9$, $R^{10}$, $R^{11}$, and $R^{12}$ are independently hydrogen, alkyl, haloalkyl, cycloalkyl, cycloalkylalkyl, aryl, aralkyl, heteroaryl, or heteroaralkyl) wherein the aromatic or alicyclic ring in $R^2$ is optionally substituted with one, two, or three $R^a$ independently selected from alkyl, haloalkyl, alkoxy, hydroxy, haloalkoxy, halo, carboxy, alkoxycarbonyl, amino, monosubstituted amino, disubstituted amino, nitro, aryloxy, benzyloxy, acyl, or arylsulfonyl and further where the aromatic or alicyclic ring in $R^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or $R^1$ and $R^2$ taken together with the carbon atom to which both $R^1$ and $R^2$ are attached form (i) cycloalkylene optionally substituted with one or two $R^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl or (ii) heterocyclylalkylene optionally substituted with one to four $R^c$ which are independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —$S(O)_{n2}R^{14}$, -alkylene-$S(O)_{n2}$—$R^{15}$, —$COOR^{16}$, -alkylene-$COOR^{17}$, —$CONR^{18}R^{19}$, or -alkylene-$CONR^{20}R^{21}$ (where n2 is 0-2 and $R^{14}$-$R^{17}$, $R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl) wherein the aromatic or alicyclic ring in the groups attached to cycloalkylene or heterocyclylalkylene is optionally substituted with one, two, or three substituents independently selected from alkyl, haloalkyl, alkoxy, hydroxy, haloalkoxy, halo, carboxy, alkoxycarbonyl, amino, monosubstituted amino, disubstituted amino, or acyl;

$R^3$ is hydrogen or alkyl;

$R^4$ is alkyl, haloalkyl, cycloalkylalkyl, aryl, aralkyl, heteroaryl, heteroaralkyl, heterocyclylalkyl, or -alkylene-$X^1$—$R^{22}$ wherein $X^1$ is $NR^{23}$, —O—, —$S(O)_{n3}$—, —CO—, —COO—, —OCO—, —$NR^{23}CO$—, —$CONR^{23}$—, —$NR^{23}SO_2$—, —$SO_2NR^{23}$—, —$NR^{23}COO$—, —$OCONR^{23}$—, —$NR^{23}CONR^{24}$—, or —$NR^{23}SO_2NR^{24}$— (where $R^{23}$ and $R^{24}$ are independently hydrogen, alkyl, or acyl and n3 is 0-2) and $R^{22}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl wherein said alkylene chain in -alkylene-$X^1$—$R^{22}$ is optionally substituted with one to six halo and wherein the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl; or $R^3$ and $R^4$ together with the carbon atom to which they are attached form cycloalkylene;

$R^5$ is hydrogen or alkyl;

$R^6$ is cycloalkyl, aryl, aralkyl, heteroaryl, heteroaralkyl, or heterocyclyl wherein the aromatic or alicyclic rings in $R^6$ are optionally substituted by one, two, or three $R^e$ independently selected from alkyl, halo, hydroxy, alkoxy, haloalkyl, haloalkoxy, oxo, cyano, nitro, acyl, aryl, aralkyl, heteroaryl, heteroaralkyl, heterocyclyl, cycloalkyl, cycloalkylalkyl, carboxy, alkoxycarbonyl, —$B(OH)_2$, or 4,4,5,5-tetramethyl-[1,3,2]dioxaborolan-2-yl and further where the aromatic or alicyclic rings in $R^e$ is optionally substituted by one, two or three $R^f$ independently selected from alkyl, alkoxy, haloalkyl, alkylthio, alkylsulfonyl, aminosulfonyl, haloalkoxy, halo, hydroxy, carboxy, cyano, nitro, aryl or cycloalkyl;

$R^7$ is haloalkyl; and $R^8$ is hydrogen, alkyl, or haloalkyl; or a pharmaceutically acceptable salt thereof, which process comprises:

(A)

(1) reacting a compound of formula (a):

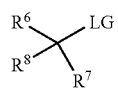

(a)

where $R^6$, $R^7$, and $R^8$ are as defined for the compound of Formula (I) above and LG is a leaving group, with a compound of formula (b):

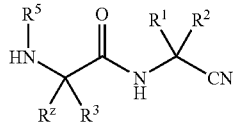
(b)

where $R^1$, $R^2$, $R^3$ and $R^5$ are as defined for the compound of Formula (a) above and $R^z$ is $R^4$ or -alkylene-$X^1$—Z where $X^1$ and $R^4$ are as defined for the compound of Formula (I) above and Z is a protecting group; to provide a compound of Formula (I) when $R^z$ is $R^4$; or a compound of formula (Ia):

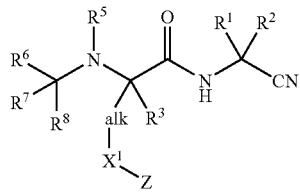
(Ia)

where $R^1$, $R^2$, $R^3$, $R^5$-$R^8$, $X^1$, and Z are as defined above;

(i) optionally modifying any of the $R^1$, $R^2$, $R^3$, and $R^5$-$R^8$ group(s) in the compound of formula (Ia);

(ii) removing the Z group in the compound of formula (Ia) obtained in Step (i) above, to give the corresponding compound of Formula (I) where $R^4$ is -alkylene-$X^1$H;

(iii) converting the compound obtained in Step (ii) above, to a compound of Formula (I) where $R^4$ is -alkylene-$X^1$—$R^{22}$ where $R^{22}$ is as defined for the compound of Formula (I) above except $R^{22}$ is other than hydrogen;

(iv) optionally modifying any of the $R^1$-$R^8$ group(s) in a compound of Formula (I) to provide a corresponding compound of Formula (I);

(v) optionally forming an acid addition salt of a compound of Formula (I); or (vi) optionally forming a free base of a compound of Formula (I); or (2) reacting a compound of formula (a) with a compound of formula (b'):

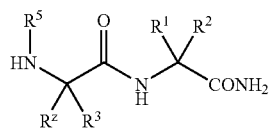
(b')

where $R^1$, $R^2$, $R^3$ and $R^5$ are as defined for the compound of Formula (I) above and $R^z$ is $R^4$ or -alkylene-$X^1$—Z where $X^1$ and $R^4$ are as defined for the compound of Formula (I) above and Z is a protecting group; to provide a compound of formula (Ib) or (Ic):

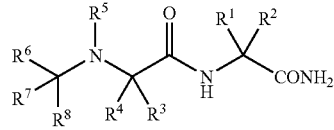
(Ib)

where $R^1$-$R^8$ are as defined for compound of Formula (I) above;

or

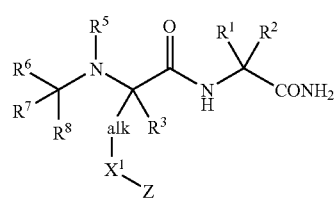
(Ic)

where $R^1$, $R^2$, $R^3$, $R^5$-$R^8$, $X^1$, and Z are as defined above;

(i) optionally modifying any of the $R^1$-$R^8$ group(s) in the compound of formula (Ib) or (Ic) to provide a corresponding compound of formula (Ib) or (Ic);

(ii) optionally removing the Z group from the compound of formula (Ic) to give a compound of Formula (Ib) where $R^4$ is -alkylene-$X^1$H;

(iii) optionally converting the compound obtained in Step (ii) above, to a compound of formula (Ib) where $R^4$ is -alkylene-$X^1$—$R^{22}$ where $R^{22}$ is as defined for the compound of Formula (I) above except $R^{22}$ is other than hydrogen;

(iv) converting the —CONH$_2$ group to —CN group in the compound (Ib) and (Ic) to provide a compound of Formula (I) and formula (Ia) respectively;

(v) optionally modifying any of the $R^1$, $R^2$, $R^3$, $R^4$, and $R^5$-$R^8$ group(s) in compound of formula (Ia);

(vi) removing the Z group from compound of formula (Ia) obtained in Step (iv) or (v) above, to give a compound of Formula (I) where $R^4$ is -alkylene-$X^1$H;

(vii) converting the compound obtained in Step (vi) above, to a compound of Formula (I) where $R^4$ is -alkylene-$X^1$—$R^{22}$ where $R^{22}$ is as defined for the compound of Formula (I) above except $R^{22}$ is other than hydrogen;

(viii) optionally modifying any of the $R^1$-$R^8$ group(s) in a compound of Formula (I) to provide a corresponding compound of Formula (I);

(ix) optionally forming an acid addition salt of a compound of Formula (I); or (x) optionally forming a free base of a compound of Formula (I); or (B)

(1) reacting a compound of formula (a):

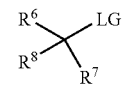
(a)

where $R^6$, $R^7$, and $R^8$ are as defined for the compound of Formula (I) above, with an amino acid of formula (c):

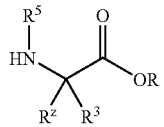
(c)

where:

R is hydrogen or a carboxy protecting group;

$R^3$ and $R^5$ are as defined for the compound of Formula (I) above; and $R^z$ is $R^4$ or -alkylene-$X^1$—Z where $X^1$ and $R^4$ are as defined for the compound of Formula (I) above and Z is a protecting group; to provide a compound of formula (d):

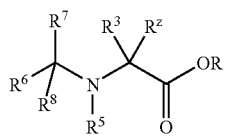
(d)

where R, $R^3$, $R^z$, $R^5$, $R^6$, $R^7$, and $R^8$ are as defined above;

(i) optionally modifying any of the $R^4$, $R^5$, $R^6$, $R^7$, and $R^8$ group(s) in the compound (d) obtained in Step (1) above;

(ii) optionally removing the Z group from compound (d) when $R^z$ is -alkylene-$X^1$—Z in the compound obtained in Step (1) or (i) above, to give a compound of formula (d) where $R^z$ is $R^4$ where $R^4$ is -alkylene-$X^1$H;

(iii) optionally converting the compound obtained in Step (ii) above, to a compound of formula (d) where $R^z$ is $R^4$ where $R^4$ is -alkylene-$X^1$—$R^{22}$ where $R^{22}$ is as defined for the compound of Formula (I) above except $R^{22}$ is other than hydrogen;

(iv) optionally modifying any of the $R^4$, $R^5$, $R^6$, $R^7$, and $R^8$ group(s) in the compound obtained from Step (iii) above;

(v) deprotecting the carboxy group in the compound obtained from Step (1), (i), (iii), or (iv) above, where R is a carboxy protecting group to provide the corresponding compound of formula (d) where R is hydrogen;

(vi) converting the acid obtained in Step (1), (i), (ii), (iii), (iv), or (v) above, where R is hydrogen to an activated acid derivative;

(vii) reacting the activated acid derivative from Step (vi) above, with a compound of formula (e) or as salt thereof:

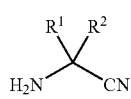
(e)

where $R^1$ and $R^2$ are as defined for the compound of Formula (I) above to provide a compound of Formula (I) when $R^z$ is $R^4$; or a compound of formula (Ia):

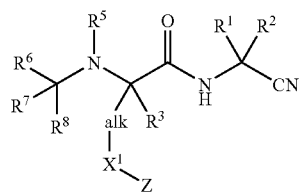
(Ia)

(viii) optionally modifying any of the $R^1$, $R^2$, $R^3$, $R^4$, and $R^6$-$R^8$ group(s) in compound of formula (Ia);

(ix) removing the Z group from compound of formula (Ia) obtained in Step (vii) or (viii) above, to give the corresponding compound of Formula (I) where $R^4$ is -alkylene-$X^1$H;

(x) converting the compound obtained in Step (ix) above, to a compound of Formula (I) where $R^4$ is -alkylene-$X^1$—$R^{22}$ where $R^{22}$ is as defined for the compound of Formula (I) above except $R^{22}$ is other than hydrogen;

(xi) optionally modifying any of the $R^1$-$R^8$ group(s) in a compound of Formula (I) to provide the corresponding compound of Formula (I);

(xii) optionally forming an acid addition salt of a compound of Formula (I); or (xiii) optionally forming a free base of a compound of Formula (I); or (2) reacting the activated acid derivative from Step (vi) above, with a compound of formula (e') or as salt thereof:

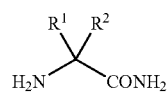
(e')

where $R^1$ and $R^2$ are as defined for the compound of Formula (I) above to provide a compound of formula (Ib) or (Ic):

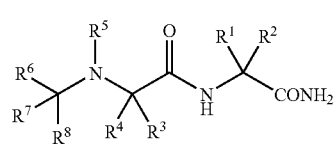
(Ib)

or

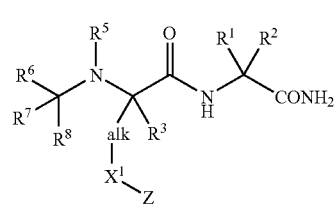
(Ic)

(i) optionally modifying any of the $R^1$-$R^8$ group(s) in a compound of formula (Ib) or (Ic) to provide a corresponding compound of formula (Ib) or (Ic);

(ii) optionally removing the Z group from compound of formula (Ic) to give the corresponding compound of formula (Ib) where $R^4$ is -alkylene-$X^1$H;

(iii) optionally converting the compound obtained in Step (ii) above, to a compound of formula (Ib) where $R^4$ is -alkylene-$X^1$—$R^{22}$ where $R^{22}$ is as defined for the compound of Formula (I) above except $R^{22}$ is other than hydrogen;

(iv) converting the —$CONH_2$ group to —CN group in the compound (Ib) and (Ic) to provide a compound of Formula (I) or formula (Ia);

(v) optionally modifying any of the $R^1$, $R^2$, $R^3$, $R^4$, and $R^6$-$R^8$ group(s) in a compound of formula (Ia);

(vi) removing the Z group in the compound of formula (Ia) obtained in Step (iv) or (v) above, to give a compound of Formula (I) where $R^4$ is -alkylene-$X^1$H;

(vii) converting the compound obtained in Step (vi) above, to a compound of Formula (I) where $R^4$ is -alkylene-$X^1$—$R^{22}$ where $R^{22}$ is as defined for the compound of Formula (I) above except $R^{22}$ is other than hydrogen;

(viii) optionally modifying any of the $R^1$-$R^8$ group(s) in a compound of Formula (I) to provide the corresponding compound of Formula (I);

(ix) optionally forming an acid addition salt of a compound of Formula (I); or (x) optionally forming a free base of a compound of Formula (I); or (C)

(1) reacting a compound of formula (a):

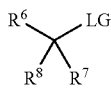

(a)

where $R^6$, $R^7$, and $R^8$ are as defined for a compound of Formula (I) above, with an amino alcohol of formula (f):

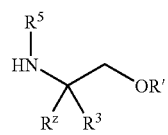

(f)

where:

R' is hydrogen or a hydroxy protecting group;

$R^3$ and $R^5$ are as defined for the compound of Formula (I) above;

$R^z$ is as defined for the compound of formula (c) above; to provide a compound of formula (g):

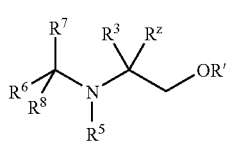

(g)

where R, $R^3$, $R^z$, $R^5$, $R^6$, $R^7$, and $R^8$ are as defined above;

(i) optionally modifying any of the $R^4$, $R^5$, $R^6$, $R^7$, and $R^8$ group(s) in the compound (g) obtained from Step (1) above;

(ii) removing the Z group in compound (g) when $R^z$ is -alkylene-$X^1$—Z obtained in Step (1) or (i) above, to give a compound of formula (g) where $R^z$ is $R^4$ where $R^4$ is -alkylene-$X^1$H;

(iii) converting the compound obtained in Step (ii) above, to a compound of formula (g) where $R^z$ is $R^4$ where $R^4$ is -alkylene-$X^1$—$R^{22}$ where $R^{22}$ is as defined for the compound of Formula (I) above except $R^{22}$ is other than hydrogen;

(iv) optionally modifying any of the $R^4$, $R^5$, $R^6$, $R^7$, and $R^8$ group(s) in the compound obtained from Step (iii) above;

(v) deprotecting the hydroxy group in the compound obtained from Step (1), (i), (iii), or (iv) above, where R' is a hydroxy protecting group and $R^z$ is $R^4$ to give a compound of formula (g) where R' is hydrogen;

(vi) converting the compound obtained in Step (1), (i), (ii), (iii), (iv), or (v) above, where R' is hydrogen to a compound of formula (h):

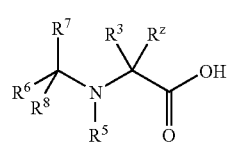

(h)

where $R^z$ is $R^4$ as defined in Formula (I) above and $R^3$, $R^5$, $R^6$, $R^7$, and $R^8$ are as defined in Formula (I) above using an oxidizing reagent;

(vii) converting compound obtained from Step (vi) above, to an activated acid derivative;

(viii) reacting activated acid derivative with a compound of formula (e) or a salt thereof:

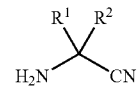

(e)

where $R^1$ and $R^2$ are as defined for Formula (I) above to provide a compound of Formula (I);

(ix) optionally modifying any of the $R^1$-$R^8$ groups to provide a corresponding compound of Formula (I);

(x) optionally forming an acid addition salt of a compound of Formula (I); and (xi) optionally forming a free base of a compound of Formula (I); or (2) reacting the activated acid derivative from Step (vii) above, with a compound of formula (e') or a salt thereof:

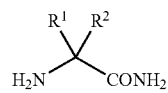

(e')

where $R^1$ and $R^2$ are as defined for the compound of Formula (I) above to provide a compound of formula (Ib):

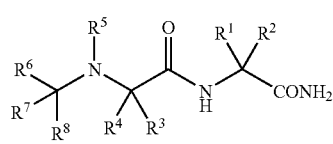

(Ib)

(i) optionally modifying any of the $R^1$-$R^8$ group(s) to provide a corresponding compound of formula (I');

(ii) converting the —$CONH_2$ group to —CN group in the compound from Step (i) above to provide a compound of Formula (I);

(iii) optionally modifying any of the $R^1$-$R^8$ group(s) to provide a corresponding compound of Formula (I);

(iv) optionally forming an acid addition salt of a compound of Formula (I); or (v) optionally forming a free base of a compound of Formula (I);

provided that LG is not bromo, mesylate, tosylate, p-nitrophenylsulfonate or 2,4-dinitrophenylsulfonate.

Preferably, LG, i.e., the leaving group, in compound (a) is trifluoromethylsulfonate or nonafluorobutylsulfonate, more preferably trifluoromethylsulfonate.

Preferably, the carboxy protecting group in compound (c) is alkyl, more preferably methyl.

Preferably, the hydroxy protecting group in compound (f) is trimethylsilyl or tert-butyldimethylsilyl.

Preferably, the conversion of (g) to (h) is carried out using suitable oxidizing agent such as $H_5IO_6/CrO_3$.

Preferably, the reaction of (a) with (b), (b') (c), and (f) is carried out in a suitable organic solvent, including but not limited to, halogenated solvent such as dichloromethane, dibromoethane, chloroform, carbon tetrachloride, and the like, ethereal solvent such as diethyl ether, tetrahydrofuran, and the like, acetonitrile, aromatic organic solvents such as benzene, toluene, xylene, and the like, or mixtures thereof and optionally in the presence of an organic or inorganic base. Preferably, the organic base is triethylamine, pyridine, N-methylmorpholine, collidine, diisopropylethylamine, and the like. Preferably, the inorganic base is cesium carbonate, sodium carbonate, sodium bicarbonate, and the like. The reaction is optionally carried out in the presence of a drying agent such as molecular sieves. Alternatively, the reaction can be carried out in neat organic base such as triethylamine, pyridine, N-methylmorpholine, collidine, diisopropylethylamine, and the like. Preferably, the reaction is carried out at a suitable reaction temperature. Preferably, the reaction is carried out between from about –78° C. to about 150° C. More preferably, the reaction is carried out at room temperature.

Preferably, the conversion of —$CONH_2$ group to cyano group in compounds of formula (I') is carried out using dehydrating agent such as $POCl_3$, trifluoroacetic anhydride, cyanuric chloride, and the like.

Preferably, the coupling of the acid with (e) or (e') is preferably carried out by generating the activated acid derivative in situ by reacting the acid with a compound of formula (e) in the presence of a suitable coupling agent e.g., benzotriazole-1-yloxytrispyrrolidino-phosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), 1,3-dicyclohexyl-carbodiimide (DCC), an the like, optionally in the presence of 1-hydroxybenzotriazole (HOBT), and in the presence of a base such as N,N-diisopropylethylamine, triethylamine, N-methylmorpholine, and the like. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Preferably, the compound of Formula (I) is prepared by Method (B).

Preferably, in the compounds above:

$R^1$ and $R^2$ are hydrogen or $R^1$ and $R^2$ taken together with the carbon atom to which both $R^1$ and $R^2$ are attached form cycloalkylene, more preferably, $R^1$ and $R^2$ taken together with the carbon atom to which both $R^1$ and $R^2$ are attached form cyclopropylene.

Preferably, $R^1$ and $R^2$ are hydrogen or $R^1$ and $R^2$ taken together with the carbon atom to which both $R^1$ and $R^2$ are attached form cycloalkylene, more preferably, $R^1$ and $R^2$ taken together with the carbon atom to which both $R^1$ and $R^2$ are attached form cyclopropylene; and $R^3$, $R^5$ and $R^8$ are hydrogen.

Preferably, $R^1$ and $R^2$ are hydrogen or $R^1$ and $R^2$ taken together with the carbon atom to which both $R^1$ and $R^2$ are attached form cycloalkylene, more preferably, $R^1$ and $R^2$ taken together with the carbon atom to which both $R^1$ and $R^2$ are attached form cyclopropylene;

$R^3$, $R^5$ and $R^8$ are hydrogen; and $R^6$ is aryl or heteroaryl wherein the aromatic rings in $R^6$ are optionally substituted by one, two, or three $R^e$ independently selected from alkyl, halo, hydroxy, alkoxy, haloalkyl, haloalkoxy, oxo, cyano, nitro, acyl, aryl, aralkyl, heteroaryl, heteroaralkyl, heterocyclyl, cycloalkyl, cycloalkylalkyl, carboxy, or alkoxycarbonyl where the aromatic or alicyclic rings in $R^e$ is optionally substituted by one, two or three $R^f$ independently selected from alkyl, alkoxy, haloalkyl, alkylthio, alkylsulfonyl, aminosulfonyl, haloalkoxy, halo, hydroxy, carboxy, cyano, nitro, aryl or cycloalkyl. More preferably, $R^6$ is phenyl optionally substituted with one, two or three $R^e$ independently selected from methyl, ethyl, chloro, fluoro, hydroxyl, methoxy, ethoxy, trifluoromethyl, trifluoromethoxy, acetyl, phenyl, thienyl, pyridinyl, furanyl, pyrrolyl, imidazolyl, cyclopropyl, cyclopentyl, cyclohexyl, carboxy, or methoxycarbonyl where the phenyl thienyl, pyridinyl, furanyl, pyrrolyl, or imidazolyl ring in $R^e$ is optionally substituted with one, two or three $R^f$ independently selected from methyl, methoxy, trifluoromethyl, methylthio, methylsulfonyl, aminosulfonyl, trifluoromethoxy, chloro, fluoro, or hydroxyl.

Preferably, $R^1$ and $R^2$ are hydrogen or $R^1$ and $R^2$ taken together with the carbon atom to which both $R^1$ and $R^2$ are attached form cycloalkylene, more preferably, $R^1$ and $R^2$ taken together with the carbon atom to which both $R^1$ and $R^2$ are attached form cyclopropylene;

$R^3$, $R^5$ and $R^8$ are hydrogen;

$R^6$ is aryl or heteroaryl, heteroaralkyl wherein the aromatic rings in $R^6$ are optionally substituted by one, two, or three $R^e$ independently selected from alkyl, halo, hydroxy, alkoxy, haloalkyl, haloalkoxy, oxo, cyano, nitro, acyl, aryl, aralkyl, heteroaryl, heteroaralkyl, heterocyclyl, cycloalkyl, cycloalkylalkyl, carboxy, or alkoxycarbonyl where the aromatic or alicyclic rings in $R^e$ is optionally substituted by one, two or three $R^f$ independently selected from alkyl, alkoxy, haloalkyl, alkylthio, alkylsulfonyl, aminosulfonyl, haloalkoxy, halo, hydroxy, carboxy, cyano, nitro, aryl or cycloalkyl. More preferably, $R^6$ is phenyl optionally substituted with one, two or three $R^e$ independently selected from methyl, ethyl, chloro, fluoro, hydroxyl, methoxy, ethoxy, trifluoromethyl, trifluoromethoxy, acetyl, phenyl, thienyl, pyridinyl, furanyl, pyrrolyl, imidazolyl, cyclopropyl, cyclopentyl, cyclohexyl, carboxy, or methoxycarbonyl where the phenyl thienyl, pyridinyl, furanyl, pyrrolyl, or imidazolyl ring in $R^e$ is optionally substituted with one, two or three $R^f$ independently selected from methyl, methoxy, trifluoromethyl, methylthio, methylsulfonyl, aminosulfonyl, trifluoromethoxy, chloro, fluoro, or hydroxyl; and $R^4$ is:

(i) alkyl, preferably 2-methylpropyl or n-propyl; or (ii) haloalkyl, preferably, 2-fluoro-2-methylpropyl, 2-trifluoromethylpropyl, 3-fluoro-2-(2-fluoromethyl)propyl, 2,2-difluoroethyl, 2,2-difluoropropyl, or 3,3,3-trifluoropropyl; or (iii) $R^4$ is aralkyl, heteroaralkyl, heterocyclylalkyl, or -alkylene-$X^1$—$R^{22}$ wherein $X^1$ is —$NR^{23}$—, —O—, —$S(O)_{n3}$—, —CO—, —COO—, —OCO—, —$NR^{23}CO$—, —$CONR^{23}$—, —$NR^{23}SO_2$—, —$SO_2NR^{23}$—, —$NR^{23}COO$—, —$OCONR^{23}$—, —$NR^{23}CONR^{24}$, or —$NR^{23}SO_2NR^{24}$— (where $R^{23}$ and $R^{24}$ are independently hydrogen, alkyl, or acyl and n3 is 0-2) and $R^{22}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl wherein said alkylene chain is optionally substituted with one to six halo and wherein the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl. Preferably, $R^4$ is benzyl, 4-methoxybenzyl, 3,4-dichlorobenzyl, 2-chlorobenzyl, 4-ethoxybenzyl, 4-nitrobenzyl, biphen-4-ylmethyl, naphth-1-ylmethyl, naphth-2-ylmethyl, 4-chlorobenzyl, 3-chlorobenzyl, 4-fluorobenzyl, 2-phenethyl, 4-hydroxybenzyl, 2-(4-hydroxy-phenyl)ethyl, 2,6-difluorobenzyl, 2,2-difluoro-3-phenylpropyl, 2,2-dichloro-3-phenylpropyl, (cyanomethylmethylcarbamoyl)methyl, biphenyl-3-ylmethyl, naphth-2-yl, 3-phenylpropyl, 2,2-difluoro-3-phenylpropyl, or 2,2-dimethyl-3-phenylpropyl.

Preferably, $R^4$ is benzenesulfonylmethyl, 2-phenylsulfanylethyl, 2-phenylsulfonyl-ethyl, naphth-2-ylmethanesulfonylmethyl, phenylmethanesulfanylmethyl, phenylmethanesulfinylmethyl, phenylmethanesulfonylmethyl, 2-phenylmethanesulfonylethyl, 4-tert-butylphenylmethanesulfonylmethyl, 2-fluorophenylmethanesulfanylmethyl, 2-fluorophenylmethanesulfonylmethyl, 3-fluorophenylmethanesulfonylmethyl, 4-fluorophenylmethanesulfonylmethyl, 2-chlorophenylmethanesulfanylmethyl, 2-chlorophenylmethanesulfonylmethyl, 3-chlorophenylmethanesulfonylmethyl, 4-chlorophenylmethanesulfonylmethyl, 2-methoxyphenylmethanesulfonylmethyl, 4-methoxyphenylmethanesulfonylmethyl, 2-trifluoromethoxyphenylmethanesulfonylmethyl, 3-trifluoromethoxyphenylmethanesulfonylmethyl, 4-trifluoromethoxyphenylmethane-sulfonylmethyl, 2-trifluoromethylphenylmethanesulfanylmethyl, 2-trifluoromethylphenylmethanesulfonylmethyl, 3-trifluoromethylphenylmethanesulfonylmethyl, 4-trifluoromethylphenylmethanesulfonylmethyl, 2-cyanophenylmethanesulfanylmethyl, 2-cyanophenylmethanesulfonylmethyl, 3-cyanophenylmethanesulfonylmethyl, 2-bromophenylmethanesulfonylmethyl, 2-nitrophenylmethanesulfanylmethyl, 2-nitrophenylmethanesulfonylmethyl, 2-methylphenylmethanesulfonylmethyl, 3-methylphenylmethanesulfonylmethyl, 4-methylphenylmethanesulfonylmethyl, 2-(4-trifluoromethoxy-benzenesulfonyl)ethyl, 2-(3-trifluoromethoxybenzenesulfonyl)-ethyl, 2-(2-trifluoromethoxy-benzenesulfonyl)-ethyl, 2-difluoromethoxyphenylmethanesulfonylmethyl, 3-difluoromethoxyphenylmethanesulfonylmethyl, 4-difluoromethoxyphenylmethanesulfonylmethyl, 2-(4-difluoromethoxybenzene-sulfonyl)ethyl, 2-(2-difluoromethoxybenzene-sulfonyl)ethyl, 2-(3-difluoromethoxybenzenesulfonyl)ethyl, 3-chloro-2-fluorophenylmethanesulfonylmethyl, 3,5-dimethylphenylmethanesulfonylmethyl, 3,5-bis-trifluoromethylphenyl-methanesulfonylmethyl, 2,5-difluorophenylmethane-sulfonylmethyl, 2,6-difluorophenylmethanesulfonylmethyl, 2,3-difluorophenylmethane-sulfonylmethyl, 3,4-difluorophenylmethanesulfonylmethyl, 2,4-difluorophenylmethane-sulfonylmethyl, 2,5-dichlorophenylmethanesulfonylmethyl, 3,4-dichlorophenylmethane-sulfonylmethyl, 2,6-dichlorophenylmethanesulfonylmethyl, 2-fluoro-3-methylphenylmethane-sulfonylmethyl, 4-fluoro-2-trifluoromethoxyphenylmethanesulfonylmethyl, 2-fluoro-6-trifluoromethylphenyl-methanesulfonylmethyl, 2-fluoro-3-trifluoromethylphenyl-methanesulfonylmethyl, 2-fluoro-4-trifluoromethylphenylmethanesulfonylmethyl, 2-fluoro-5-trifluoromethyl-phenylmethanesulfonylmethyl, 4-fluoro-3-trifluoromethyl-phenylmethanesulfonylmethyl, 2-chloro-5-trifluoromethylphenylmethane-sulfonylmethyl, 2,4,6-trifluorophenylmethane-sulfonylmethyl, 2,4,5-trifluorophenylmethanesulfonylmethyl, 2,3,4-trifluorophenylmethanesulfonylmethyl, 2,3,5-trifluorophenylmethanesulfonylmethyl, 2,5,6-trifluorophenylmethanesulfonyl-methyl, 3,4,5-trimethoxyphenylmethane-sulfonylmethyl, pyridin-2-ylmethanesulfonylmethyl, pyridin-3-ylmethanesulfonylmethyl, pyridin-4-ylmethanesulfonylmethyl, 2-(pyridin-2-ylsulfonyl)ethyl, 2-(pyridin-4-ylsulfonyl)ethyl, N-oxypyridin-2-ylmethanesulfonylmethyl, 6-trifluoromethylpyridin-2-ylmethanesulfonylmethyl, pyrazin-2-ylmethanesulfonylmethyl, cyclohexylmethanesulfanylmethyl, cyclohexylmethane-sulfinylmethyl, cyclohexylmethanesulfonylmethyl, 2-cyclohexylethanesulfonyl, cyclohexylmethanesulfonylmethyl, cyclopropylmethanesulfonylmethyl, thiophene-2-sulfonylmethyl, 5-chlorothien-2-ylmethanesulfonylmethyl, or 3,5-dimethylisoxazol-4-ylmethanesulfonylmethyl.

Most preferably, $R^4$ is isopropylsulfonylmethyl, cyclopropylmethanesulfonylmethyl, 2-phenylsulfonylethyl, pyridin-4-ylsulfonylmethyl, pyridin2-ylmethanesulfonylmethyl, pyridin-3-ylmethanesulfonylmethyl, 6-trifluoromethylpyridin-2-ylmethanesulfonylmethyl, benzylsulfonylmethyl i.e., phenylmethanesulfonylmethyl, 2-(difluoromethoxy)phenylmethanesulfonylmethyl, or pyrazin-2-ylmethylsulfonylmethyl.

Within the above preferred groups and more, even more, and most preferred groups contained therein, particularly preferred group of compounds are those wherein $R^7$ is difluoromethyl or trifluoromethyl, more preferably trifluoromethyl.

It will be readily apparent to a person of ordinary skill in the art that groups that are reactive under a given set of reaction conditions will be protected during those reactions and then deprotected later. For example, a compound of Formula (I) where the aromatic ring is substituted with reactive group(s) such as amino, hydroxy, and the like, or groups containing such groups may be synthesized using starting materials where such groups are suitably protected and then later deprotected; or they can be prepared from other groups. For example, compound of Formula (I) containing an amino group or a derivative thereof within the scope of this invention can be prepared by using starting material carrying a nitro group which can then be reduced to an amino group or a derivative thereof.

Preferably, this invention is directed to a process of preparing a compound of Formula (I):

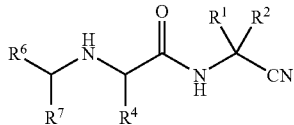
(I)

wherein:

$R^1$ and $R^2$ taken together with the carbon atom to which both $R^1$ and $R^2$ are attached form cyclopropylene;

$R^4$ is alkyl, haloalkyl, or —$CH_2$—$SO_2$—$R^{22}$ wherein $R^{22}$ is cycloalkylalkyl, aralkyl, or heteroaralkyl wherein the aromatic or alicyclic ring in $R^4$ is optionally substituted with one, two, or three $R^d$ independently selected from alkyl, haloalkyl, alkoxy, hydroxy, haloalkoxy, or halo;

$R^6$ is aryl optionally substituted with one, two, or three $R^e$ independently selected from alkyl, halo, hydroxy, alkoxy, haloalkyl, haloalkoxy, —$B(OH)_2$, 4,4,5,5-tetramethyl-[1,3,2]dioxaborolan-2-yl, or aryl where the aromatic ring in $R^e$ is optionally substituted with $R^f$ where $R^f$ is alkylthio or alkylsulfonyl; and $R^7$ is haloalkyl; or a pharmaceutically acceptable salt thereof; which process comprises:

(1) reacting a compound of formula:

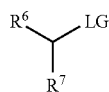
(a)

where:

LG is a leaving group; and $R^6$ is aryl optionally substituted with one, two, or three $R^e$ independently selected from alkyl, halo, alkoxy, haloalkyl, haloalkoxy, or aryl where the aromatic ring in $R^e$ is optionally substituted with $R^f$ where $R^f$ is alkylthio or alkylsulfonyl and $R^7$ are as defined for the compound of Formula (I) above; with a compound of formula (c):

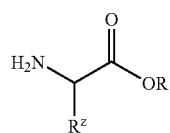
(c)

where:

R is hydrogen or a carboxy protecting group; and $R^z$ is alkyl, haloalkyl, or —$CH_2$—S—$R^{22}$ where $R^{22}$ is as defined for Formula (I) above; to form a compound of formula (d):

(d)

where R, $R^z$, $R^6$, and $R^7$ are as defined above;

(i) optionally converting $R^z$ to $CH_2$—$SO_2$—$R^{22}$ when $R^z$ is —$CH_2$—S—$R^{22}$ and/or $R^e$ and/or $R^f$ group(s) to a group as defined for the compound of Formula (I) above;

(ii) deprotecting the carboxy group in the compound obtained from Step (1) or (i) where R is a carboxy protecting group;

(iii) optionally converting $R^z$ to —$CH_2$—$SO_2$—$R^{22}$ when $R^z$ is —$CH_2$—S—$R^{22}$ and/or $R^e$ and/or $R^f$ group(s) to a group as defined for the compound of Formula (I) above;

(iv) converting the compound from Step (1), (i), (ii), or (iii) above where R is hydrogen, to an activated acid derivative;

(v) reacting the activated acid derivative from Step (iv) above, with a compound of formula (e) or a salt thereof:

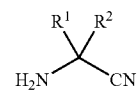
(e)

where $R^1$ and $R^2$ are as defined for a compound of Formula (I) above to provide a compound of Formula (I) where $R^z$ is $R^4$ or a compound of formula (I):

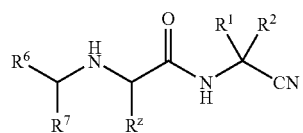
(i)

where $R^1$, $R^2$, $R^6$, $R^7$ as defined above and $R^z$ is —$CH_2$—S—$R^{22}$ where $R^{22}$ is as defined above;

(vi) converting —$CH_2$—S—$R^{22}$ to —$CH_2$—$SO_2$—$R^{22}$ in compound (i) with an oxidizing agent to give a compound of Formula (I);

(vii) optionally modifying any of the $R^e$ and/or $R^{22}$ group(s) in a compound of Formula (I) to provide the corresponding compound of Formula (I);

(viii) optionally forming an acid addition salt of a compound of Formula (I); or (ix) optionally forming a free base of a compound of Formula (I); provided that it LG is not halo, mesylate, tosylate, p-nitrophenyl-sulfonate or 2,4-dinitrophenylsulfonate in the compound of formula (a). Preferably, the carboxy protecting group is alkyl, preferably methyl. Preferably, the deprotection of the carboxy group (i.e., R) is carried out under basic hydrolysis reaction conditions utilizing a suitable base such as sodium hydroxide, lithium hydroxide, cesium hydroxide, and the like, in a suitable solvent such as aqueous alcoholic solvent such as aqueous methanol, ethanol, and the like.

Preferably, reaction of (a) with (c) is carried out under the reaction conditions described above.

Preferably, conversion of $R^z$ to —$CH_2$—$SO_2$—$R^{22}$ is carried out using oxidizing agent such as OXONE®, m-chloroperbenzoic acid. Preferably, the conversion of methylthio group to methylsulfonyl is carried out with $Na_2WO_4 \cdot H_2O$ and $Bu_4NHSO_4$ in the presence of hydrogen peroxide, and the like.

Preferably, the reaction of the acid (R is hydrogen) is carried out by generating the activated acid derivative in situ by reacting the acid with a compound of formula (e) in the presence of a suitable coupling agent e.g., benzotriazole-1-yloxytrispyrrolidino-phosphonium hexafluorophosphate (PyBOP®), O-benzotriazol-1-yl-N,N,N',N'-tetramethyl-uronium hexafluorophosphate (BBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), 1,3-dicyclohexyl-carbodiimide (DCC), an the like, optionally in the presence of 1-hydroxybenzotriazole (HOBT), and in the presence of a base such as N,N-diisopropylethylamine, triethylamine, N-methylmorpholine, and the like. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Preferably, this invention is directed to a process of preparing a compound of Formula (I):

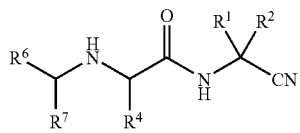

(I)

wherein:

$R^1$ and $R^2$ taken together with the carbon atom to which both $R^1$ and $R^2$ are attached form cyclopropylene;

$R^4$ is —$CH_2$—$SO_2$—$R^{22}$ wherein $R^{22}$ is cycloalkylalkyl, aralkyl, or heteroaralkyl wherein the aromatic or alicyclic ring in $R^4$ is optionally substituted with one, two, or three $R^d$ independently selected from alkyl, haloalkyl, alkoxy, hydroxy, haloalkoxy, or halo;

$R^6$ is aryl optionally substituted by one, two, or three $R^e$ independently selected from alkyl, halo, hydroxy, alkoxy, or haloalkyl; and $R^7$ is haloalkyl; or a pharmaceutically acceptable salt thereof; which process comprises:

A (1) reacting a compound of formula:

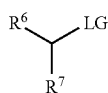

(a)

where:

LG is trifluoromethanesulfonate or nonfluorobutylsulfonate;

$R^6$ and $R^7$ are as defined for the compound of Formula (I) above; with a compound of formula (c):

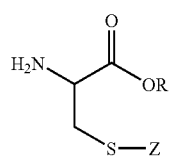

(c)

where:

R is hydrogen or a carboxy protecting group and Z is a thiol protecting group; to provide a compound of formula (d):

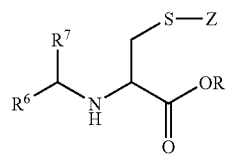

(d)

where Z, R, $R^6$, and $R^7$ are as defined above;

(i) removing the thiol protecting group Z to provide a compound of formula (j);

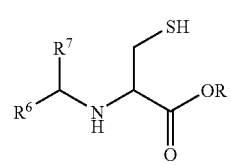

(j)

where R, $R^6$, and $R^7$ are as defined above;

(ii) converting the compound from Step (i) above to a compound of formula (k):

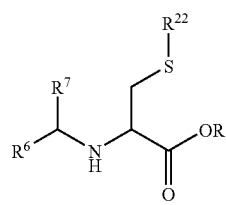

(k)

where R, $R^6$, $R^7$, and $R^{22}$ is as defined above;

(iii) optionally converting the compound from Step (iii) above to a compound of formula (1):

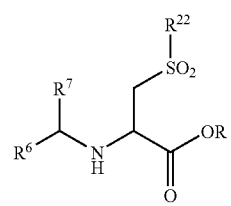

(l)

where R, $R^6$, $R^7$, and $R^{22}$ is as defined above;

(iv) deprotecting the carboxy group in the compound obtained from Step (ii) or (iii) above, where R is a carboxy protecting group;

(v) converting the compound from Step (iv) above to an activated acid derivative;

(vi) reacting the activated acid derivative from Step (v) above, with a compound of formula (e) or a salt thereof:

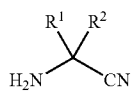

(e)

where $R^1$ and $R^2$ are as defined for the compound of Formula (I) above to provide a compound of Formula (I); or a compound of formula (m);

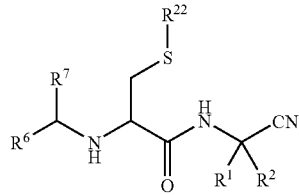

(m)

(vii) converting —$CH_2$—S—$R^{22}$ to —$CH_2$—$SO_2$—$R^{22}$ in compound (m) to give a compound of Formula (I);

(ix) optionally modifying any of the $R^d$ and/or $R^{22}$ group(s) in compound of Formula (I) to provide a corresponding compound of Formula (I);

(x) optionally forming an acid addition salt of a compound of Formula (I); or (xi) optionally forming a free base of a compound of Formula (I); or (B)

(1) removing the carboxy protecting group in compound (d) where R is a carboxy protecting group to provide a compound of formula (d) where R is hydrogen;

(i) converting the compound from Step (1) above to an activated acid derivative;

(ii) reacting the activated acid derivative from Step (i) above, with a compound of formula (e) or a salt thereof:

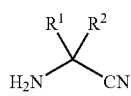

(e)

where $R^1$ and $R^2$ are as defined for the compound of Formula (I) above to provide a compound of formula (n);

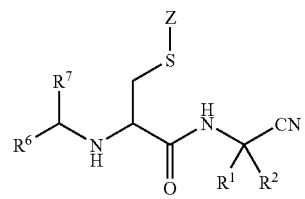

(n)

(iii) removing the thiol protecting group Z in (n) to give the corresponding compound of formula (o);

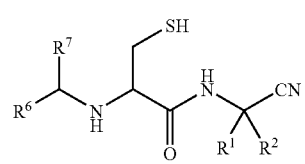

(o)

(iv) converting the compound from Step (iii) above to a compound of formula (p):

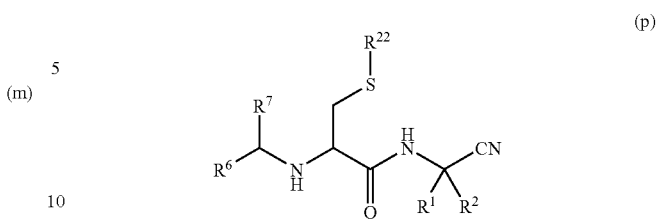

(p)

where R, $R^6$, $R^7$, and $R^{22}$ is as defined above;

(v) converting —$CH_2$—S—$R^{22}$ to —$CH_2$—$SO_2$—$R^{22}$ in compound (p) to give a compound of Formula (I);

(vi) optionally modifying any of the $R^d$ and/or $R^{22}$ group(s) in compound of Formula (I) to provide a corresponding compound of Formula (I);

(vii) optionally forming an acid addition salt of a compound of Formula (I); or (vii) optionally forming a free base of a compound of Formula (I).

Preferably, the thiol protecting groups are trityl, diphenylmethyl wherein the phenyl group(s) is optionally substituted with one, two, or three substitutents independently selected from alkyl, halo, alkoxy, haloalkyl, or hydroxy, preferably, trityl or diphenylmethyl. Other thiol protecting groups include —CONHR where R is alkyl or substituted or unsubstituted aryl, preferably ethyl or —C(O)OR where R is benzyl or substituted benzyl. Other suitable thiol protecting group can be found in groups can be found in T. W. Greene, *Protecting Protective Groups in Organic Synthesis*, 3rd edition, John Wiley & Sons, Inc. 1999, the disclosure of which is incorporated herein by reference in its entirety.

Preferably, the reaction of (a) with (c) and (d) with (e) are carried out as described above. Preferably the solvent is halogenated organic solvent. Preferably, R is hydrogen or alkyl, more preferably hydrogen. The compound of Formula (I) is preferably carried out by procedure (A).

Preferably, this invention is directed to a process of preparing a compound of Formula (I):

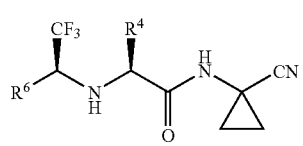

(I)

wherein:

$R^4$ is —$CH_2$—$SO_2$—$R^{22}$ wherein $R^{22}$ is phenylmethanesulfonylmethyl, cyclopropylmethanesulfonylmethyl, pyrazin-2-ylmethanesulfonylmethyl, 6-trifluoropyridin-2-ylmethanesulfonylmethyl, 2-difluoromethoxyphenylmethanesulfonylmethyl, or pyridin-2-yl-methanesulfonylmethyl; and $R^6$ is phenyl or 4-fluorophenyl; or a pharmaceutically acceptable salt thereof; which process comprises:

(A) (1) reacting a compound of formula (a):

(a)

where:

LG is trifluoromethanesulfonate or nonfluorobutylsulfonate; and

R⁶ is phenyl or 4-fluorophenyl; with a compound of formula (c):

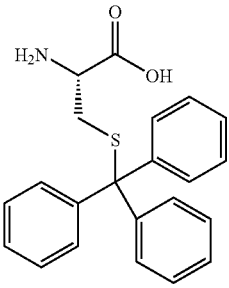
(c)

to form a compound of formula (d):

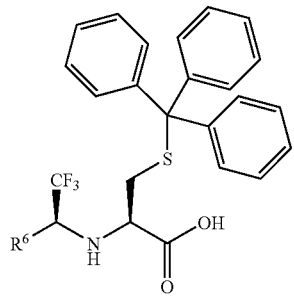
(d)

where R⁶ is as defined above;

(ii) removing the thiol protecting group;

(iii) reacting the compound from Step (ii) above, with R²²X where X is a leaving group and R²² is phenylmethyl, cyclopropylmethyl, pyrazin-2-ylmethyl, 2-trifluoropyridin-2-ylmethyl, 2-difluoromethoxyphenylmethyl, or pyridin-2-ylmethyl to provide a compound of formula:

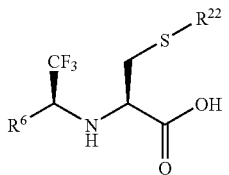
(k)

where R²² is as defined above;

(iv) optionally oxidizing the thiol group in (k) to sulfone;

(v) converting the compound from Step (iii) or (iv) above, to an activated acid derivative;

(vi) reacting the activated acid derivative from step (v) above, with a compound of formula (e) or a salt thereof:

(e)

to provide a compound of Formula (I); or a compound of formula (q):

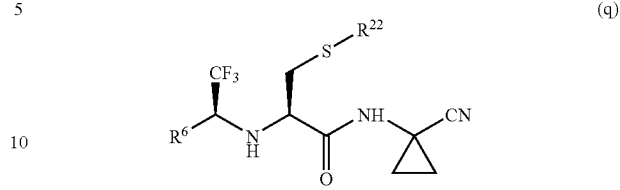
(q)

(vii) oxidizing the thiol group in (q) to sulfone to give a compound of Formula (I);

(viii) optionally forming an acid addition salt of a compound of Formula (I); or (ix) optionally forming a free base of a compound of Formula (I).

Preferably, the oxidation of sulfur to sulfone is carried out prior to coupling with (e) i.e., Step (iv).

Preferably, the reaction of (a) with (c) is carried out in a suitable organic solvent, including but not limited to, halogenated solvent such as dichloromethane, dibromoethane, chloroform, carbon tetrachloride, and the like, ethereal solvent such as diethyl ether, tetrahydrofuran, and the like, acetonitrile, aromatic organic solvents such as benzene, toluene, xylene, and the like, or mixtures thereof and optionally in the presence of an organic or inorganic base. Preferably, the organic base is triethylamine, pyridine, N-methylmorpholine, collidine, diisopropylethylamine, and the like. Preferably, the inorganic base is cesium carbonate, sodium carbonate, sodium bicarbonate, and the like. The reaction is optionally carried out in the presence of a drying agent such as molecular sieves. Alternatively, the reaction can be carried out in neat organic base such as triethylamine, pyridine, N-methylmorpholine, collidine, diisopropylethylamine, and the like. Preferably, the reaction is carried out at a suitable reaction temperature. Preferably, the reaction is carried out between from about –78° C. to about 150° C. More preferably, the reaction is carried out at room temperature.

The trityl protecting group is removed with an acid in the presence of a reducing agent. Preferably, the deprotection is done using trifluoroacetic acid in the presence of triethylsilane in a suitable organic solvent such as halogenated organic solvent.

The thiol is oxidized with a suitable oxidizing agent described above, preferably OXONE®.

The coupling of the acid with (e) is preferably carried out by generating the activated acid derivative in situ by reacting the acid with a compound of formula (e) in the presence of a suitable coupling agent e.g., benzotriazole-1-yloxytrispyrrolidino-phosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), 1,3-dicyclohexyl-carbodiimide (DCC), an the like, optionally in the presence of 1-hydroxybenzotriazole (HOBT), and in the presence of a base such as N,N-diisopropylethylamine, triethylamine, N-methylmorpholine, and the like. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Preferably, in $R^{22}X$, X is halo, tosylate, mesylate, triflate, and the like. More preferably X is halo, even more preferably bromo. The reaction is carried out in the presence of a base such as sodium hydroxide, lithium hydroxide, cesium carbonate, and the like, either in aqueous medium or a mixture of aqueous/polar organic solvent such as alcoholic solvent such as methanol, ethanol, and the like, DMF, dioxane, THF, and the like.

Preferably, the compounds prepared by the above processes are:

N-(1-cyanocyclopropyl)-3-phenylmethanesulfonyl-2(R)-(2,2,2-trifluoro-1(S)-phenylethylamino)-propionamide;

N-(4-cyano-1-ethylpiperidin-4-yl)-3-(phenylmethanesulfonyl-2(R)-(2,2,2-trifluoro-1(S)-phenyl-ethylamino)propionamide;

N-(4-cyano-1,1-dioxohexahydro-1$\lambda^6$-thiopyran-4-yl)-3-phenylmethanesulfonyl-2(R)-(2,2,2-trifluoro-1(S)-phenylethylamino)-propionamide;

N-(1-cyanocyclopropyl)-3-phenylmethanesulfanyl-2(R)-(2,2,2-trifluoro-1(S)-4-hydroxyphenyl-ethylamino)propionamide;

N-(1-cyanocyclopropyl)-3-cyclopropylmethanesulfonyl-2(R)-(2,2,2-trifluoro-1(S)-phenylethyl-amino)propionamide;

N-(1-cyanocyclopropyl)-3-phenylmethanesulfanyl-2(R)-(2,2,2-trifluoro-1(RS)-furan-2-ylethyl-amino)propionamide;

N-(1-cyanocyclopropyl)-3-phenylmethanesulfonyl-2(R)-(2,2,2-trifluoro-1(RS)-furan-2-ylethyl-amino)propionamide;

N-(1-cyanocyclopropyl)-3-cyclopropylmethanesulfonyl-2(R)-(2,2,2-trifluoro-1(S)-3-bromophenyl-ethylamino)propionamide;

N-(1-cyanocyclopropyl)-3-phenylmethanesulfanyl-2(R)-(2,2,2-trifluoro-1(RS)-indol-3-ylethyl-amino)propionamide;

N-(1-cyanocyclopropyl)-3-phenylmethanesulfonyl-2(R)-(2,2,2-trifluoro-1(RS)-indol-3-ylethyl-amino)propionamide;

N-(1-cyanocyclopropyl)-3-phenylmethanesulfanyl-2(R)-(2,2,2-trifluoro-1(RS)-thiophen-2-ylethyl-amino)propionamide;

N-(1-cyanocyclopropyl)-3-phenylmethanesulfonyl-2(R)-(2,2,2-trifluoro-1 (RS)-thiophen-2-ylethyl-amino)propionamide;

N-(1-cyanocyclopropyl)-3-cyclopropylmethanesulfonyl-2(R)-(2,2,2-trifluoro-1(S)-4-fluorophenyl-ethylamino)propionamide;

N-(1-cyanocyclopropyl)-3-phenylmethanesulfonyl-2(R)-(2,2,2-trifluoro-1(S)-methylethylamino)-propionamide;

N-(1-cyanocyclopropyl)-3-phenylmethanesulfonyl-2(R)-(2,2,2-trifluoro-1(S)-1-methylpyrrol-2-yl-ethylamino)propionamide;

N-(1-cyanocyclopropyl)-3-(1-methylcyclopentyl)-2(S)-(2,2,2-trifluoro-1(S)-thiophen-2-ylethyl-amino)propionamide;

N-(1-cyanocyclopropyl)-3-(1-methylcyclopentyl)-2(S)-(2,2,2-trifluoro-1(R)-thiophen-2-ylethyl-amino)propionamide;

N-(1-cyanocyclopropyl)-3-phenylmethanesulfonyl-2(R)-(2,2,2-trifluoro-1(S)-4-fluorophenylethyl-amino)propionamide;

N-(1-cyanocyclopropyl)-3-pyridin-2-ylmethanesulfanyl-2(R)-(2,2,2-trifluoro-1(RS)-phenylethyl-amino)propionamide;

N-(1-cyanocyclopropyl)-3-pyridin-2-ylmethanesulfonyl-2(R)-(2,2,2-trifluoro-2(S)-phenylethyl-amino)propionamide;

N-(1-cyanocyclopropyl)-3-(1-methylcyclopentyl)-2(S)-(2,2,2-trifluoro-1(S)-2-hydroxyphenyl-ethylamino)propionamide;

N-(1-cyanocyclopropyl)-3-(1-methylcyclopentyl)-2(S)-(2,2,2-trifluoro-1(R)-4-hydroxyphenyl-ethylamino)propionamide;

N-(1-cyanocyclopropyl)-3-pyridin-2-ylmethanesulfonyl-2(R)-(2,2,2-trifluoro-1(R)-phenylethyl-amino)propionamide;

N-(1-cyanocyclopropyl)-3-(1-methylcyclopentyl)-2(S)-(2,2,2-trifluoro-1(S)-4-hydroxyphenyl-ethylamino)propionamide;

N-(1-cyanocyclopropyl)-3-(2-chlorophenyl)-2(S)-(2,2,2-trifluoro-1 (RS)-phenylethylamino)-propionamide;

N-(1-cyanocyclopropyl)-3-(2-chlorophenyl)-2(1)-(2,2,2-trifluoro-1(RS)-4-fluorophenyl-ethylamino)-propionamide;

N-(1-cyanocyclopropyl)-3-pyridin-2-ylmethanesulfonyl-2(R)-(2,2,2-trifluoro-1(RS)-4-fluorophenyl-ethylamino)propionamide;

N-(1-cyanocyclopropyl)-3-phenylmethanesulfonyl-2(R)-(2,2,2-trifluoro-1(S)-4-hydroxyphenyl-ethylamino)propionamide;

N-(1-cyanocyclopropyl)-3-phenylmethanesulfanyl-2(R)-(2,2,2-trifluoro-1(R)-3-chloro-4-hydroxy-phenylethylamino)propionamide;

N-(1-cyanocyclopropyl)-3-phenylmethanesulfanyl-2(R)-(2,2,2-trifluoro-1(S)-3-chloro-4-hydroxy-phenylethylamino)propionamide;

N-(1-cyanocyclopropyl)-3-phenylmethanesulfonyl-2(R)-(2,2,2-trifluoro-1(R)-3-chloro-4-hydroxy-phenylethylamino)propionamide;

N-(1-cyanocyclopropyl)-3-phenylmethanesulfonyl-2(R)-(2,2,2-trifluoro-1(S)-3-chloro-4-hydroxy-phenylethylamino)propionamide;

N-(1-cyanocyclopropyl)-3-(1-methylcyclopentyl)-2(S)-(2,2-difluoro-1(R)-thiophen-2-ylethyl-amino)propionamide;

N-(1-cyanocyclopropyl)-3-phenylmethanesulfanyl-2(R)-(2,2-difluoro-1(RS)-thiophen-2-ylethyl-amino)propionamide;

N-(1-cyanocyclopropyl)-3-(1-methylcyclopentyl)-2(S)-(2,2,2'-trifluoro-1(S)-3-fluoro-4-hydroxy-phenylethylamino)propionamide;

N-(1-cyanocyclopropyl)-3-phenylmethanesulfanyl-2(R)-(2,2,2-trifluoro-1(RS)-pyridin-2-ylethyl-amino)propionamide;

N-(1-cyanocyclopropyl)-4-pyridin-2-ylsulfanyl-2(O)-(2,2,2-trifluoro-1(RS)-4-fluorophenyl-ethylamino)butyramide;

N-(1-cyanocyclopropyl)-4-pyridin-2-ylsulfonyl-2(S)-(2,2,2-trifluoro-1(RS)-4-fluorophenyl-ethylamino)butyramide;

N-(1-cyanocyclopropyl)-3-phenylmethanesulfonyl-2(R)-(2,2,2-trifluoro-1(RS)-pyridin-2-yl-ethylamino)propionamide;

N-(1-cyanocyclopropyl)-3-phenylmethanesulfonyl-2(R)-(2,2-difluoro-1(R)-thiophen-2-yl-ethylamino)propionamide;

N-(1-cyanocyclopropyl)-3-(2-difluoromethoxyphenyl-methanesulfanyl)-2(R)-(2,2,2-trifluoro-1 (RS)-thiophen-2-ylethylamino)propionamide;

N-(1-cyanocyclopropyl)-3-(2-difluoromethoxyphenyl-methanesulfonyl)-2(R)-(2,2,2-trifluoro-1 (RS)-thiophen-2-ylethylamino)propionamide;

N-(1-cyanocyclopropyl)-3-pyridin-2-ylmethanesulfanyl-2(R)-(2,2,2-difluoro-1(S)-4-fluorophenyl-ethylamino)propionamide;

N-(1-cyanocyclopropyl)-3-pyridin-2-ylmethanesulfonyl-2(R)-(2,2,2-trifluoro-1(S)-4-fluorophenyl-ethylamino)propionamide;

N-(1-cyanocyclopropyl)-3-pyridin-2-ylmethanesulfanyl-2(R)-(2,2,2-trifluoro-1(R)-4-fluorophenyl-ethylamino)propionamide;

N-(1-cyanocyclopropyl)-3-pyridin-2-ylmethanesulfonyl-2 (R)-(2,2,2-trifluoro-1(R)-4-fluorophenyl-ethylamino)propionamide;

N-(1-cyanocyclopropyl)-3-cyclopropylmethanesulfonyl-2 (R)-(2,2,2-trifluoro-1(S)-thiophen-3-ylethylamino)propionamide;

N-(1-cyanocyclopropyl)-3-cyclopropylmethanesulfanyl-2 (R)-(2,2,2-trifluoro-1 (RS)-thiophen-2-yl-ethylamino)propionamide;

N-(1-cyanocyclopropyl)-3-cyclopropylmethanesulfonyl-2 (R)-(2,2,2-trifluoro-1(RS)-thiophen-2-yl-ethylamino)propionamide;

N-(1-cyanotetrahydropyran-4-yl)-3-cyclopropylmethanesulfonyl-2(R)-(2,2,2-trifluoro-1(S)-4-fluorophenylethylamino)propionamide;

N-(1-cyanocyclopropyl)-3-cyclopropylmethanesulfonyl-2 (R)-(2,2,4-trifluoro-1(S)-3,4-difluoro-phenylethylamino) propionamide;

N-(1-cyanocyclopropyl)-3-cyclopropylmethanesulfonyl-2 (R)-(2,2,2-trifluoro-1(S)-1-methylpyrrol-2-ylethylamino) propionamide;

N-(1-cyanocyclopropyl)-3-cyclopropylmethanesulfonyl-2 (R)-(2,2,2-trifluoro-1(S)-1-oxo-1-methyl-pyrrol-2-yl-ethylamino)propionamide;

N-(1-cyanocyclopropyl)-3-cyclopropylmethanesulfonyl-2 (R)-(2,2,2-trifluoro-1(S)-3,4,5-trifluoro-phenylethylamino)propionamide;

N-(1-cyanocyclopropyl)-3-(4-fluorophenylmethanesulfonyl)-2(R)-(2,2,2-trifluoro-1(S)-4-fluoro-phenylethylamino)propionamide;

N-(1-cyanotetrahydrothiopyran-4-yl)-3-(4-fluorophenylmethanesulfonyl)-2(R)-(2,2,2-trifluoro-1(S)-4-fluorophenyl-ethylamino)propionamide;

N-(1-cyanocyclopropyl)-3-(4-fluorophenylmethanesulfonyl)-2(R)-(2,2,2-trifluoro-1 (S)-3-phenoxy-phenylethylamino)propionamide;

N-(1-cyano-1,1-dioxohexahydro-1$\lambda^6$-thiopyran-4-yl)-3-(4-fluorophenylmethane-sulfonyl)-2(R)-(2,2,2-trifluoro-1 (S)-4-fluorophenylethylamino)propionamide;

N-(1-cyanocyclopropyl)-3-(2-difluoromethoxyphenyl-methanesulfonyl)-2(R)-(2,2,2-trifluoro-1 (RS)-1-phenyl-sulfonylpyrrol-2-ylethylamino)propionamide;

N-(1-cyanocyclopropyl)-3-(2-difluoromethoxyphenyl-methanesulfonyl)-2(R)-(2,2,2-trifluoro-1(S)-4-fluorophenyl-ethylamino)propionamide;

N-(1-cyanocyclopropyl)-3-(2-trifluoromethylpyridin-6-yl-methanesulfonyl)-2(R)-(2,2,2-trifluoro-1(RS)-4-fluorophenyl-ethylamino)propionamide;

N-(1-cyanocyclopropyl)-3-cyclopropylmethanesulfonyl-2 (R)-(2,2,2-trifluoro-1(RS)-1-phenyl-sulfonylpyrrol-2-yl-ethylamino)propionamide;

N-(1-cyanocyclopropyl)-3-pyrazin-2-ylmethanesulfonyl-2 (R)-(2,2,2-trifluoro-1(R)-4-fluorophenyl-ethylamino)propionamide;

N-(1-cyanocyclopropyl)-3-pyrazin-2-ylmethanesulfonyl-2 (R)-(2,2,2-trifluoro-1(S)-4-fluorophenyl-ethylamino)propionamide;

N-(1-cyanotetrahydropyran-4-yl)-3-(2-difluoromethoxyphenylmethanesulfonyl)-2(R)-(2,2,2-trifluoro-1(S)-4-fluorophenylethylamino)propionamide;

N-(1-cyano 1,1-dioxohexahydro-1$\lambda^6$-thiopyran-4-yl)-3-(2-difluoromethoxyphenyl-methanesulfonyl)-2(R)-(2,2,2-trifluoro-1(S)-4-fluorophenylethylamino)propionamide;

N-(1-cyanocyclopropyl)-3-(2-trifluoromethylpyridin-6-yl-methylmesulfonyl)-2(R)-(2,2,2-Z-trifluoro-1(S)-4-fluorophenyl-ethylamino)propionamide;

N-(1-cyanocyclopropyl)-3-pyrazin-2-ylmethanesulfanyl-2 (R)-(2,2,2-trifluoro-1(R)-4-fluorophenyl-ethylamino)propionamide;

N-(1-cyanocyclopropyl)-3-pyrazin-2-ylmethanesulfanyl-2 (R)-(2,2,2-trifluoro-1(S)-4-fluorophenyl-ethylamino)propionamide;

N-(1-cyanocyclopropyl)-3-(1-oxopyridin-2-ylmethanesulfonyl)-2(R)-(2,2,2-trifluoro-1(S)-4-fluorophenyl-ethylamino)propionamide; and N-(1-cyanocyclopropyl)-3-(pyridin-2-ylmethanesulfonyl)-2-(2,2,2-trifluoro-1-phenyl-1-trifluoromethylethylamino)-propionamide; or a pharmaceutically acceptable salt thereof.

More preferably,

N-(1-cyanocyclopropyl)-3-cyclopropylmethanesulfonyl-2 (R)-(2,2,2-trifluoro-1(S)-phenyl-ethylamino)propionamide;

N-(1-cyanocyclopropyl)-3-cyclopropylmethanesulfonyl-2 (R)-(2,2,2-trifluoro-1(S)-4-fluorophenyl-ethylamino)propionamide;

N-(1-cyanocyclopropyl)-3-pyridin-2-ylmethanesulfonyl-2 (R)-(2,2,2-trifluoro-1(S)-phenylethyl-amino)propionamide;

N-(1-cyanocyclopropyl)-3-pyridin-2-ylmethanesulfonyl-2 (R)-(2,2,2-trifluoro-1(S)-4-fluorophenyl-ethylamino)propionamide;

N-(1-cyanocyclopropyl)-3-cyclopropylmethanesulfonyl-2 (R)-(2,2,2-trifluoro-1(S)-3,4-difluoro-phenylethylamino) propionamide;

N-(1-cyanocyclopropyl)-3-(4-fluorophenylmethanesulfonyl)-2(R)-(2,2,2-trifluoro-1(S-4-fluoro-phenylethylamino)propionamide;

N-(1-cyanocyclopropyl)-3-(2-difluoromethoxyphenyl-methanesulfonyl)-2(R)-(2,2,2-trifluoro-1(S)-4-fluorophenylethylamino)propionamide;

N-(1-cyanocyclopropyl)-3-pyrazin-2-ylmethanesulfonyl-2 (R)-(2,2,2-trifluoro-1(R)-4-fluoro-phenylethylamino)propionamide; and N-(1-cyanocyclopropyl)-3-pyrazin-2-ylmethanesulfonyl-2 (R)-(2,2,2-trifluoro-1(S)-4-fluoro-phenylethylamino)propionamide; and N-(1-cyanocyclopropyl)-3-(2-trifluoromethylpyridin-6-yl-methanesulfonyl)-2(R)-(2,2,2-trifluoro-1(S)-4-fluorophenyl-ethylamino)propionamide; or a pharmaceutically acceptable salt thereof.

Preferably, this invention is directed to a process for preparing a compound of Formula (I):

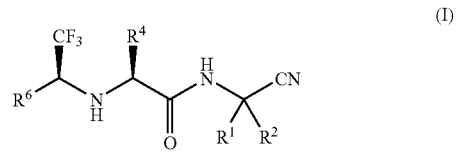

where:

$R^1$ and $R^2$ are hydrogen or $R^1$ and $R^2$ together with the carbon atom to which they are attached form cyclopropylene;

$R^4$ is 2-methylpropyl or 2-fluoro-2-methylpropyl; and $R^6$ is phenyl optionally substituted at the 4-position with halo, —B(OH)$_2$, 4,4,5,5-tetramethyl-[1.3.2]dioxaborolan-2-yl, hydroxy, 4'-methylthiobiphen-4-yl, 4'-methylsulfinylbiphen-4-yl, 4'-methylsulfonylbiphen-4-yl, or 4'-aminosulfonylbiphen-4-yl; or a pharmaceutically salt thereof; which process comprises:

(1) reacting a compound of formula (a):

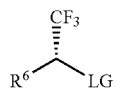

(a)

where:

LG is a leaving group, preferably trifluoromethanesulfonate or nonfluorobutylsulfonate; and $R^6$ is 4-halophenyl, 4'-methylthiobiphen-4-yl, or 4'-methylsulfonylbiphen-4-yl; with a compound of formula (r):

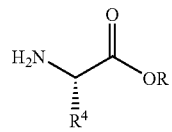

(r)

where R is hydrogen or a carboxy protecting group and $R^4$ is as defined above, to give a compound of formula (s):

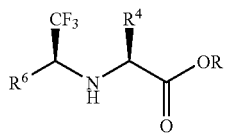

(s)

where R and $R^4$ are as defined above and $R^6$ is 4-halophenyl, 4'-methylthiobiphen-4-yl, or 4'-methylsulfonylbiphen-4-yl;

(i) optionally converting compound (s) where $R^6$ is 4-halophenyl to a corresponding compound of formula (s) where $R^6$ is 4'-methylthiobiphen-4-yl, or 4'-methylsulfonylbiphen-4-yl or 4'-aminosulfonylbiphen-4-yl;

(ii) optionally oxidizing the methylthio group in compound from Step (1) or (i) above to methylsulfinyl or methylsulfonyl;

(iii) removing the carboxy protecting group in compound obtained from Step (1), (i), or (ii) above where R is a carboxy protecting group to give free acid;

(iv) converting the compound from Step (1), (i), (ii), or (iii) above where R is hydrogen, to an activated acid derivative;

(v) reacting the activated acid derivative from Step (iv) above, with a compound of formula (e) or a salt thereof:

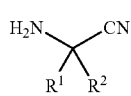

(e)

where $R^1$ and $R^2$ are as defined above, to provide a compound of Formula (I) where $R^6$ is halo, 4'-aminosulfonylbiphen-4-yl, 4'-methylthiobiphen-4-yl, 4'-methylsulfinylbiphen-4-yl, or 4'-methylsulfonylbiphen-4-yl; or (vi) reacting the activated acid derivative from Step (iv) above, with a compound of formula (e') or a salt thereof:

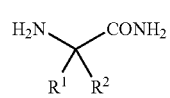

(e')

(vii) converting the —$CONH_2$ group to —CN in compound obtained from Step (vi) above to provide a compound of Formula (I) where $R^6$ is halo, 4'-aminosulfonylbiphen-4-yl, 4'-methylthiobiphen-4-yl, 4'-methylsulfinylbiphen-4-yl, or 4'-methylsulfonylbiphen-4-yl;

(viii) optionally modifying the $R^6$ group in a compound of Formula (I) to give a corresponding compound of Formula (I);

(viii) optionally forming an acid addition salt of compound (I); and (ix) optionally forming a free base of compound (I).

The reaction of (a) with (r) and (s) with (e) are be carried out as described above. Preferably, compound of Formula (I) is carried out by reacting (s) with (e).

A compound of formula (s) or (a) where $R^6$ is 4-halophenyl can be converted to a corresponding compound of formula (O) where $R^6$ is 4'-methylthiobiphen-4-yl or aminosulfonylbiphen-4-yl by reacting it with 4-methythiophenylboronic acid or 4-aminosulfonylphenylboronic acid, respectively. Alternatively, it can be converted to the corresponding boronic acid derivative and then reacted with 4-methylthiophenyl halide or 4-aminosulfonylphenyl halide.

Preferably, the compounds of Formula (I) are:

$N^1$-(1-cycanocyclopropyl)-4-fluoro-$N^2$-{1(S)-2,2,2-trifluoro-1-[4'-(methylsulfonyl)-1,1'biphenyl-4-yl]ethyl}-L-leucinamide;

$N^1$-(1-cycanocyclopropyl)-4-fluoro-$N^2$-{1(S)-2,2,2-trifluoro-1-[4'-(methylsulfinyl)-1,1'biphenyl-4-yl]ethyl}-L-leucinamide;

$N^1$-(cyanomethyl)-$N^2$-{1(S)-2,2,2-trifluoro-1-[4'-(methylsulfonyl)-1,1'biphenyl-4-yl]ethyl}-L-leucinamide; or $N^2$-{1(S)-1-[4'-(aminosulfonyl)-1,1'biphenyl-4-yl]}-2,2,2-trifluoro}-$N^1$-(cyanomethyl)-L-leucinamide; or a pharmaceutically acceptable salt thereof.

In a second aspect, this invention is directed to a process of preparing a compound of Formula (I):

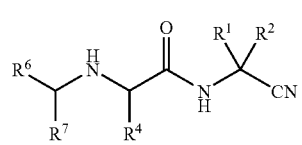

(I)

wherein:

$R^1$ and $R^2$ are hydrogen or $R^1$ and $R^2$ taken together with the carbon atom to which both $R^1$ and $R^2$ are attached form cycloalkylene, preferably cyclopropylene;

$R^4$ is —$CH_2$—$SO_2$—$R^{22}$ wherein $R^{22}$ is cycloalkylalkyl, aralkyl, or heteroaralkyl wherein the aromatic or alicyclic ring in $R^4$ is optionally substituted with one, two, or three $R^d$ independently selected from alkyl, haloalkyl, alkoxy, hydroxy, haloalkoxy, or halo;

$R^6$ is aryl optionally substituted by one, two, or three $R^e$ independently selected from alkyl, halo, hydroxy, alkoxy, or haloalkyl; and $R^7$ is haloalkyl; or a pharmaceutically acceptable salt thereof; which process comprises:

A (1) reacting a compound of formula:

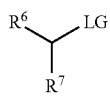

(a)

where:

LG is trifluoromethanesulfonate or nonfluorobutylsulfonate;

$R^6$ and $R^7$ are as defined for the compound of Formula (I) above; with a compound of formula (t):

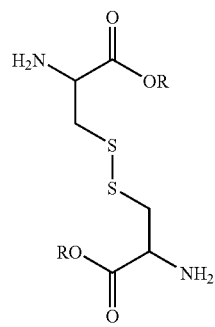

(t)

where R is hydrogen or a carboxy protecting group to provide a compound of formula (u):

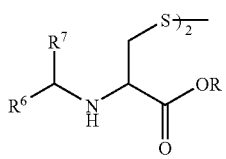

(u)

where R, $R^6$, and $R^7$ are as defined above;

(i) converting (u) to a compound of formula (v) with a reducing agent:

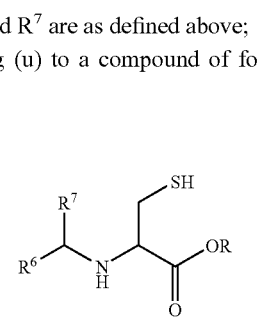

(v)

where R, $R^6$, and $R^7$ are as defined above;

(ii) converting compound (v) to a compound of formula (w):

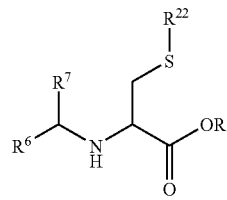

(w)

where R, $R^6$, $R^7$, and $R^{22}$ is as defined above;

(iii) optionally converting the compound from Step (ii) above to a compound of formula (x):

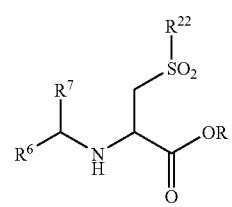

(x)

where R, $R^6$, $R^7$, and $R^{22}$ is as defined above;

(iv) deprotecting the carboxy group in the compound obtained from Step (ii) or (iii) above, where R is a carboxy protecting group;

(v) converting the compound from Step (iv) above to an activated acid derivative;

(vi) reacting the activated acid derivative from Step (v) above, with a compound of formula (e) or a salt thereof:

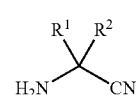

(e)

where $R^1$ and $R^2$ are as defined for the compound of Formula (I) above to provide a compound of Formula (I); or a compound of formula (x);

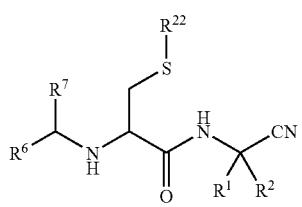

(x)

(vii) converting —$CH_2$—S—$R^{22}$ to —$CH_2$—$SO_2$—$R^{22}$ in compound (x) to give a compound of Formula (I);

(ix) optionally modifying any of the $R^d$ and/or $R^{22}$ group(s) in compound of Formula (I) to provide a corresponding compound of Formula (I);

(x) optionally forming an acid addition salt of a compound of Formula (I); or (xi) optionally forming a free base of a compound of Formula (I); or (2) reacting the activated acid derivative from Step (v) above, with a compound of formula (e') or a salt thereof:

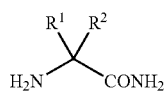

where $R^1$ and $R^2$ are as defined for the compound of Formula (I) above to provide a compound of formula (Id) or (Ie):

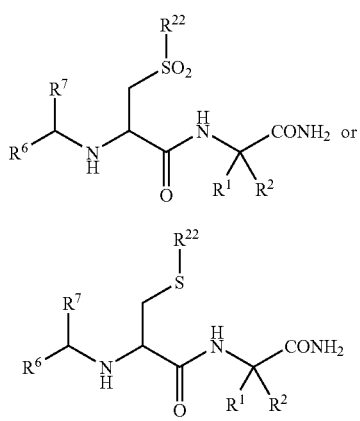

or (i) converting the —$CONH_2$ group to —CN group in the compound from Step (2) above to provide a compound of Formula (I) or a compound of formula (If):

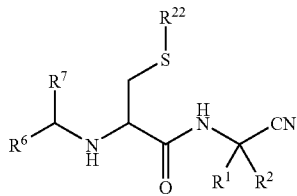

(ii) oxidizing the sulfur atom to sulfone with an oxidizing agent;
(iii) optionally modifying any of the $R^1$-$R^8$ group(s) to provide a corresponding compound of Formula (I);
(iv) optionally forming an acid addition salt of a compound of Formula (I); or
(v) optionally forming a free base of a compound of Formula (I).

In a third aspect, this invention is directed to a compound of formula (d):

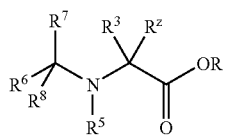

wherein:
R is hydrogen or a carboxy protecting group;
$R^3$ is hydrogen or alkyl;
$R^z$ is $R^4$ where $R^4$ is aryl, aralkyl, heteroaryl, heteroaralkyl, heterocyclylalkyl, or -alkylene-$X^1$—$R^{22}$ (wherein $X^1$ is —$NR^{23}$—, —O—, —$S(O)_{n3}$—, —CO—, —COO—, —OCO—, —$NR^{23}CO$—, —$CONR^{23}$—, —$NR^{23}SO_2$—, —$SO_2NR^{23}$—, —$NR^{23}COO$—, —$OCONR^{23}$—, —$NR^{23}CoNR^{24}$—, or —$NR^{23}SO_2NR^{24}$— where $R^{23}$ and $R^{24}$ are independently hydrogen, alkyl, or acyl, n3 is 0-2, $R^{22}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl) wherein said alkylene chain in -alkylene-$X^1$—$R^{22}$ is optionally substituted with one to six halo and wherein the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl; or -alkylene-$X^1$—Z where $X^1$ is as defined above and Z is a protecting group;
$R^5$ is hydrogen or alkyl;
$R^6$ is cycloalkyl, aryl, aralkyl, heteroaryl, heteroaralkyl, or heterocyclyl wherein the aromatic or alicyclic rings in $R^6$ are optionally substituted by one, two, or three $R^e$ independently selected from alkyl, halo, hydroxy, alkoxy, haloalkyl, haloalkoxy, oxo, cyano, nitro, acyl, aryl, aralkyl, heteroaryl, heteroaralkyl, heterocyclyl, cycloalkyl, cycloalkylalkyl, carboxy, or alkoxycarbonyl where the aromatic or alicyclic rings in $R^e$ is optionally substituted by one, two or three $R^f$ independently selected from alkyl, alkoxy, haloalkyl, alkylthio, alkylsulfonyl, aminosulfonyl, haloalkoxy, halo, hydroxy, carboxy, cyano, nitro, aryl or cycloalkyl; and
$R^7$ is haloalkyl;
$R^8$ is hydrogen, alkyl, or haloalkyl; or a salts thereof.

Preferably,
R is hydrogen or alkyl, preferably hydrogen or methyl;
$R^3$ is hydrogen;
$R^z$ is -alkylene-$S(O)_{n3}$—$R^{22}$ where n3 is 0 to 2 and $R^{22}$ is hydrogen, cycloalkylalkyl, aralkyl, or heteroaralkyl wherein the aromatic ring in $R^{22}$ is optionally substituted with one, two, or three $R^d$ independently selected from alkyl, haloalkyl, alkoxy, hydroxy, haloalkoxy, halo, nitro, cyano, carboxy, or alkoxycarbonyl; or -alkylene-S—Z where $X^1$ is as defined above and Z is a thiol protecting group;
$R^5$ is hydrogen;
$R^6$ is aryl or heteroaryl wherein the aromatic in $R^6$ are optionally substituted by one, two, or three $R^e$ independently selected from alkyl, halo, hydroxy, alkoxy, haloalkyl, haloalkoxy, oxo, cyano, nitro, or acyl; and
$R^7$ is haloalkyl;
$R^8$ is hydrogen; or a salts thereof.

Preferably, R is hydrogen or methyl; $R^3$, $R^5$, and $R^8$ are hydrogen, $R^z$ is -alkylene-S—Z where Z is a protecting group; $R^7$ is difluoromethyl or trifluoromethyl; and $R^6$ is phenyl or 4-fluorophenyl.

In a fourth aspect, this invention is directed to a compound of formula (g):

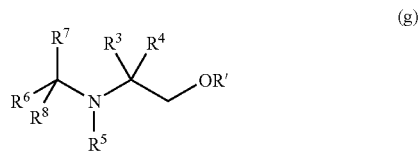

wherein:

R' is hydrogen or a hydroxy protecting group;

$R^3$ is hydrogen or alkyl;

$R^4$ is aryl, aralkyl, heteroaryl, heteroaralkyl, heterocyclylalkyl, or -alkylene-$X_—R^{22}$ wherein $X^1$ is —$NR^{23}$—, —O—, —S(O)$_{n3}$—, —CO—, —COO—, —OCO—, —$NR^{23}$CO—, —CONR$^{23}$—, —$NR^{23}$SO$_2$—, —SO$_2$NR$^{23}$—, —$NR^{23}$COO—, —OCONR$^{23}$—, —$NR^{23}$CONR$^{24}$—, or —$NR^{23}$SO$_2$NR$^{24}$— (where $R^{23}$ and $R^{24}$ are independently hydrogen, alkyl, or acyl and n3 is 0-2) and $R^{22}$ where $R^{22}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl wherein said alkylene chain in -alkylene-$X^1$—$R^{22}$ is optionally substituted with one to six halo and wherein the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl or -alkylene-$X^1$—Z where $X^1$ is as defined above and Z is a protecting group;

$R^5$ is hydrogen or alkyl;

$R^6$ is cycloalkyl, aryl, aralkyl, heteroaryl, heteroaralkyl, or heterocyclyl wherein the aromatic or alicyclic rings in $R^6$ are optionally substituted by one, two, or three $R^e$ independently selected from alkyl, halo, hydroxy, alkoxy, haloalkyl, haloalkoxy, oxo, cyano, nitro, acyl, aryl, aralkyl, heteroaryl, heteroaralkyl, heterocyclyl, cycloalkyl, cycloalkylalkyl, carboxy, or alkoxycarbonyl where the aromatic or alicyclic rings in $R^e$ is optionally substituted by one, two or three $R^f$ independently selected from alkyl, alkoxy, haloalkyl, alkylthio, alkylsulfonyl, aminosulfonyl, haloalkoxy, halo, hydroxy, carboxy, cyano, nitro, aryl or cycloalkyl;

$R^7$ is haloalkyl; and $R^8$ is hydrogen, alkyl, or haloalkyl; or a salt thereof.

Preferably, R' is hydrogen or tert-butyldimethylsilyl; $R^3$, $R^5$, and $R^8$ are hydrogen, $R^z$ is -alkylene-S—Z where Z is a protecting group; $R^7$ is difluoromethyl or trifluoromethyl; and $R^6$ is phenyl or 4-fluorophenyl.

In a fifth aspect, this invention is directed to a compound of formula (a):

wherein:

LG is trifluoromethylsulfonate or nonafluorobutylsulfonate;

$R^6$ is phenyl optionally substituted at the 4-position with halo, alkoxy, or 4-methylthiophenyl, or 4-methylsulfonylphenyl;

$R^7$ is haloalkyl; and $R^8$ is hydrogen; or a salt thereof.

Preferably, $R^7$ is trifluoromethyl.

In a sixth aspect, this invention is directed to a method of forming a compound of Formula (I):

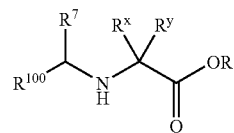

where:

R is hydrogen or a carboxy protecting group;

$R^x$ is hydrogen or alkyl;

$R^y$ is a natural or unnatural amino acid side chain or a precursor group thereof;

$R^7$ is haloalkyl; and $R^{100}$ is a substituted or unsubstituted aryl, heteroaryl, or heterocyclyl ring; or a salt thereof, which method comprises reacting a compound of formula:

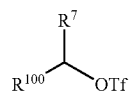

where $R^7$ and $R^{100}$ are as defined above; with an amino acid of formula:

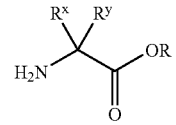

where R, $R^x$ and $R^y$ are as defined above.

Preferably, the compound of Formula (I) is as defined in the first aspect of the invention.

DETAILED DESCRIPTION OF THE INVENTION

Unless otherwise stated, the following terms used in the specification and claims are defined for the purposes of this Application and have the following meanings.

"Alicyclic" means a moiety characterized by arrangement of the carbon atoms in closed non-aromatic ring structures having properties resembling those of aliphatics e.g., cycloalkyl and heterocyclyl rings as defined herein.

"Alkyl" represented by itself means a straight or branched, saturated aliphatic radical containing one to six carbon atoms, unless otherwise indicated e.g., alkyl includes methyl, ethyl, propyl, isopropyl, butyl, sec-butyl, isobutyl, tert-butyl, and the like.

"Alk" as used in this Application refers to "alkylene" as defined herein.

"Alkylene", unless indicated otherwise, means a straight or branched, saturated aliphatic, divalent radical having the number of one to six carbon atoms, e.g., methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—)2-methyltetramethylene (—CH$_2$CH (CH$_3$)CH$_2$CH$_2$—), pentamethylene (—CH$_2$CH$_2$CH$_2$CH$_2$CH$_2$—), and the like.

"Amino" means —NH$_2$ radical. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Alkylamino" or "dialkylamino" refers to a —NHR and —NRR' radical respectively, where R and R' are independently alkyl group as defined above e.g., methylamino, dimethylamino, and the like.

"Alkoxy" refers to a —OR radical where R is an alkyl group as defined above e.g., methoxy, ethoxy, and the like.

"Alkoxycarbonyl" refers to a —C(O)OR radical where R is an alkyl group as defined above e.g., methoxycarbonyl, ethoxycarbonyl, and the like.

"Alkoxycarbonylalkyl" means an -(alkylene)-C(O)OR radical where R is alkyl as defined above e.g., methoxycarbonylmethyl, 2-, or 3-ethoxycarbonylmethyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxy" refers to a —OR radical where R is alkoxyalkyl is as defined above.

"Alkoxyalkyloxyalkyl" refers to a -(alkylene)-O-(alkylene)-OR radical where R is an alkyl group e.g., as defined above, e.g., 2-methoxyethyloxymethyl, 3-methoxypropyloxyethyl, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —COR$^a$ where R$^a$ is alkyl, and R' is hydrogen or alkyl as defined above, e.g., aminomethyl, methylaminoethyl, dimethylaminoethyl, 1,3-diaminopropyl, acetylaminopropyl, and the like.

"Aminosulfonyl" refers to a —SO$_2$R radical where R is —NRR' where R is hydrogen, alkyl, or —COR$^a$ where R$^a$ is alkyl, and R' is hydrogen or alkyl as defined above.

"Alkylthio" refers to a radical —SR where R is an alkyl group as defined above, e.g., methylthio, ethylthio, and the like.

"Alkylsulfonyl" refers to a —SO$_2$R radical where R is an alkyl group as defined above e.g., methylsulfonyl, ethylsulfonyl, and the like.

"Acyl" refers to a —COR radical where R is hydrogen, alkyl, haloalkyl, aryl, aralkyl, heteroaryl, heteroaralkyl, or heterocyclyl as defined herein, e.g., formyl, acetyl, trifluoroacetyl, benzoyl, piperazin-1-ylcarbonyl, and the like.

"Aromatic" refers to a moiety wherein the constituent atoms make up an unsaturated ring system, all atoms in the ring system are sp$^2$ hybridized and the total number of pi electrons is equal to 4n+2.

"Aryl" refers to a monocyclic or fused bicyclic ring assembly containing 6 to 10 ring carbon atoms unless otherwise indicated, wherein each ring is aromatic e.g., phenyl or napthyl.

"Aralkyl" refers to a -(alkylene)-R radical where R is aryl as defined above e.g., benzyl, phenethyl, and the like.

"Aryloxy" refers to a —OR radical where R is aryl as defined above e.g., phenoxy, and the like.

"Aryloxyalkyl" refers to a -(alkylene)-OR radical where R is aryl as defined above e.g., phenoxymethyl, 2-, or 3-phenoxymethyl, and the like "Aryloxycarbonyl" refers to a —C(O)OR radical where R is aryl as defined above e.g., phenyloxycarbonyl, and the like.

"Arylsulfonyl" refers to a —SO$_2$R radical where R is an aryl group as defined above e.g., phenylsulfonyl, and the like.

"Carboxy" refers to —C(O)OH radical.

"Carboxyalkyl" refers to a -(alkylene)-C(O)OH radical e.g., carboxymethyl, carboxyethyl, and the like.

"Cycloalkyl" refers to a monovalent saturated or partially unsaturated, monocyclic, fused bicyclic or bridged polycyclic ring assembly containing three to eight ring carbon atoms e.g., cyclopropyl, cyclobutyl, cyclopentyl, cyclohexyl, cyclohexenyl, 2,5-cyclohexadienyl, bicyclo[2.2.2]octyl, adamantan-1-yl, and the like.

"Cycloalkylalkyl" refers to a -(alkylene)-R radical where R is cycloalkyl as defined above e.g., cyclopropylmethyl, cyclobutylethyl, cyclobutylmethyl, and the like "Cycloalkylene" refers to a divalent saturated or, partially unsaturated or fully unsaturated (provided that it is not aromatic) monocyclic ring or bridged polycyclic ring assembly containing three to eight ring carbon atoms. For example, the instance wherein "R$^1$ and R$^2$ together with the carbon atom to which both R$^1$ and R$^2$ are attached form cycloalkylene" includes, but is not limited to, the following:

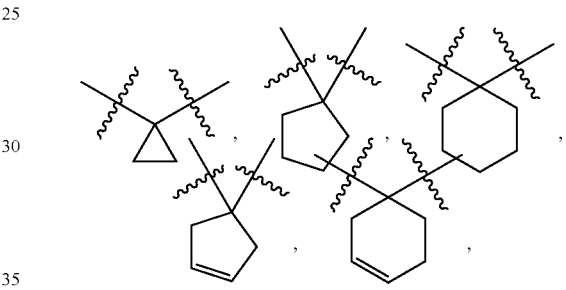

and the like.

"Disubstituted amino" refers to a —NRR' radical where R is alkyl, aryl, aralkyl, heteroaryl, or heteroaralkyl, or heterocyclyl and R' is alkyl, aryl, aralkyl, heteroaryl, heteroaralkyl, cycloalkyl, heterocyclyl, cycloalkylalkyl, hydroxyalkyl, alkoxyalkyl, or acyl as defined herein. Representative examples include, but are not limited to, dimethylamino, methylphenylamino, benzylmethylamino, acetylmethylamino, and the like.

"Halo" refers to fluoro, chloro, bromo or iodo.

"Haloalkyl" refers to alkyl as defined above substituted by one or more, preferably one to five, "halo" atoms, as such terms are defined in this Application. Haloalkyl includes monohaloalkyl, dihaloalkyl, trihaloalkyl, perhaloalkyl and the like e.g. chloromethyl, dichloromethyl, difluoromethyl, trifluoromethyl, 2,2,2-trifluoroethyl, perfluoroethyl, 2,2,2-trifluoro-1,1-dichloroethyl, and the like).

"Haloalkoxy" refers to a —OR radical where R is haloalkyl group as defined above e.g., trifluoromethoxy, 2,2,2-trifluoroethoxy, difluoromethoxy, and the like.

"Heteroaryl" as a group or part of a group denotes an aromatic monocyclic or multicyclic moiety of 5 to 10 ring members atoms in which one or more, preferably one, two, or three, of the ring members is/are element atom(s) is (other than carbon, for example are) selected from nitrogen, oxygen or sulfur, the remaining ring atoms being carbon. Representative heteroaryl rings include, but are not limited to, pyrrolyl, furanyl, thienyl, oxazolyl, isoxazolyl, thiazolyl, imidazolyl, triazolyl, tetrazolyl, pyridinyl, pyrimidinyl, pyrazinyl, pyridazinyl, indolyl, benzofuranyl, benzothienyl, benzimidazolyl, quinolinyl, isoquinolinyl, quinazolinyl, quinoxalinyl, pyrazolyl, and the like.

"Heteroaralkyl" refers to a -(alkylene)-R radical where R is heteroaryl as defined above e.g., pyridinylmethyl, 1- or 2-furanylethyl, imidazolylmethyl, and the like.

"Heteroaryloxyalkyl" refers to a -(alkylene)-OR radical where R is heteroaryl as defined above e.g., furanyloxymethyl, 2-, or 3-indolyloxyethyl, and the like.

"Heterocyclyl" refers to a saturated or partially unsaturated, mono or bicyclic radical of 4, 5, or 6 carbon ring atoms wherein cycloalkyl, as defined in this Application, provided that one or more, preferably one, or two, or three of the ring carbon atoms indicated are replaced by a heteroatom moiety selected from —N═, —N—, —O—, —CO—, —S—, —SO—, or —S(O)$_2$— and further wherein one or two ring atoms are optionally replaced by a keto (—CO—) group. The heterocyclyl ring is optionally fused to cycloalkyl, aryl or heteroaryl ring as defined herein. Representative examples include, but are not limited to, imidazolidinyl, morpholinyl, thiomorpholinyl, thiomorpholino-1-oxide, thiomorpholino-1,1-dioxide, tetrahydropyranyl, tetrahydrothiopyranyl, 1-oxo-tetrahydrothiopyranyl, 1,1-dioxotetrathiopyranyl, indolinyl, piperazinyl, piperidyl, pyrrolidinyl, pyrrolinyl, quinuclidinyl, and the like.

"Heterocyclylalkyl" refers to a -(alkylene)-heterocyclyl radical as defined in this Application. Representative examples include, but are not limited to, imidazolidin-1-ylmethyl, morpholin-4-ylmethyl, thiomorpholin-4-ylmethyl, thiomorpholin-4-ylmethyl-1-oxide, indolinylethyl, piperazinylmethyl or ethyl, piperidylmethyl or ethyl, pyrrolidinylmethyl or ethyl, and the like.

"Heterocyclylalkylene" refers to a divalent heterocyclylalkyl group, as defined in this Application, provided that one or more, preferably one or two, of the ring member carbon atoms indicated, is replaced by heteroatom moiety selected from —N═, —N—, —O—, —S— or —S(O)$_2$—. For example e.g., the instance wherein $R^1$ and $R^2$ together with the carbon atom to which both $R^1$ and $R^2$ are attached form heterocycloalkyleneheterocyclylalkylene" includes, but is not limited to, the following:

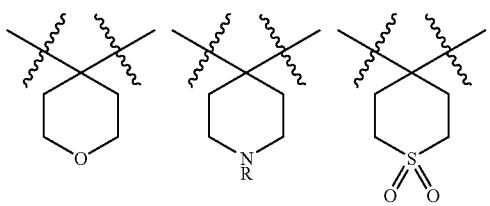

in which R is a substituent defined in the Summary of the Invention

"Hydroxy" means —OH radical. Unless indicated otherwise, the compounds of the invention containing hydroxy radicals include protected derivatives thereof. Suitable protecting groups for hydroxy moieties include benzyl and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Isomers" mean compounds of Formula (I) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula (I) are meant to be encompassed all possible stereoisomers.

"Keto or oxo" means (═O) radical.

"Leaving group" has the meaning conventionally associated with it in synthetic organic chemistry i.e., an atom or group capable of being displaced by a nucleophile and includes halogen, alkanesulfonyloxy, arenesulfonyloxy, ester, or amino such as chloro, bromo, iodo, mesyloxy, tosyloxy, trifluorosulfonyloxy, methoxy, N,O-dimethylhydroxylamino, and the like.

"Activated acid derivative" has the meaning conventionally associated with it in synthetic organic chemistry i.e., an ester, acid halide, amide, acyl azide, acyl cyanide, or anhydride derivative of the carboxylic acid group that has greater reactivity than the free —COOH group.

"Monosubstituted amino" refers to a —NHR radical where R is alkyl, aryl, aralkyl, heteroaryl, heteroaralkyl, cycloalkyl, cycloalkylalkyl, hydroxyalkyl, alkoxyalkyl, or acyl as defined herein. Representative examples include, but are not limited to, methylamino, phenylamino, benzylamino, cycloalkylmethylamino, acetylamino, trifluoroacetyl, and the like.

"Nitro" means —NO$_2$ radical.

"Optional" or "optionally" or "may be" means that the subsequently described event or circumstance may or may not occur, and that the description includes instances where the event or circumstance occurs and instances in which it does not. For example, the phrase "wherein the aromatic ring $R^4$ is optionally substituted . . . with one or two substituents independently selected from alkyl" means that the aromatic ring in $R^4$ may or may not be substituted with alkyl in order to fall within the scope of the invention.

The present invention also includes N-oxide derivatives of a compound of Formula (I). N-oxide derivative mean a compound of Formula (I) in which a nitrogen atom is in an oxidized state (i.e., N→O) e.g., pyridine N-oxide, and which possess the desired pharmacological activity.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (I) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Protected derivatives" means derivatives of compounds of Formula (I) in which a reactive site or sites are blocked with protecting groups. Protected derivatives of compounds of Formula (I) are useful in the preparation of compounds of Formula (I). A comprehensive list of suitable protecting groups can be found in T. W. Greene, *Protecting Protective Groups in Organic Synthesis*, 3rd edition, John Wiley & Sons, Inc. 1999.

"Precursor group" refers to any group that can be converted to a natural or unnatural amino acid side chain.

The expression " ... wherein said alkylene chain in $R^4$ or $R^6$ is optionally substituted ." in the Summary of the Invention refers to the alkylene chain in -alkylene-$X^1$—$R^{22}$ and -alkylene-$X^2$—$R^{25}$ respectively, being optionally substituted.

The expression " ... wherein the aromatic or alicyclic ring in $R^2$, $R^4$, or $R^6$ is optionally substituted with one to three $R^a$, $R^d$, or $R^e$ respectively ... " refers to all the groups attached to $R^2$, $R^4$, or $R^6$ that contain an aromatic or alicyclic ring being optionally substituted with one to three $R^a$, $R^d$, or $R^e$ respectively, e.g., for $R^4$ it includes the aromatic or alicyclic ring in the cycloalkyl, cycloalkylalkyl, aryl, aralkyl, heteroaryl, heteroaralkyl, heterocyclylalkyl, or -alkylene-$X^1$—$R^{22}$ (wherein $X^1$ is —$NR^{23}$—, —O—, —$S(O)_{n3}$—, —CO—, —COO—, —OCO—, —$NR^{23}CO$—, —$CONR^{23}$—, —$NR^{23}SO_2$—, —$SO_2NR^{23}$—, —$NR^{23}COO$—, —$OCOONR^{23}$—, —$NR^{23}CONR^{24}$—, or —$NR^{23}SO_2NR^{24}$— where $R^{23}$ and $R^{24}$ are independently hydrogen, alkyl, or acyl, n3 is 0-2, and $R^{22}$ is cycloalkyl, cycloalkylalkyl, heterocyclyl, aryl, aralkyl, heteroaryl, or heteroaralkyl, heterocyclyl, or heterocyclylalkyl) groups being optionally substituted with $R^d$.

Synthetic Schemes

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of the Invention can be prepared via the synthetic processes illustrated and described below.

Method (A)

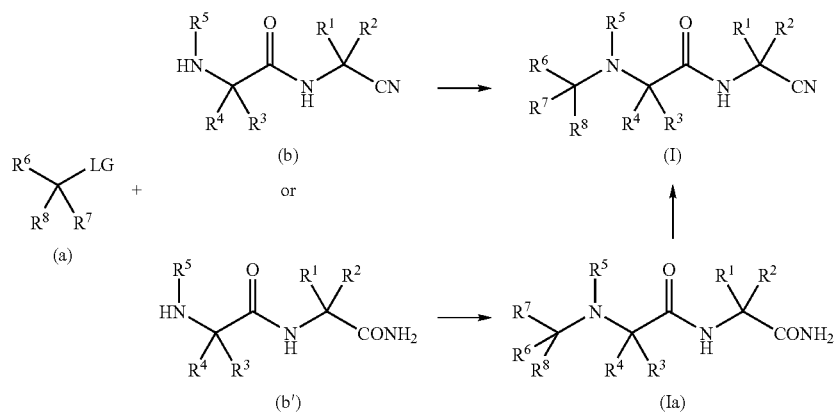

In Method (A), reaction of a compound of formula (a) where LG is a suitable leaving group such as trifluoromethansulfonate, and the like, and $R^6$, $R^7$, and $R^8$ are as defined in Summary of the Invention with a compound of formula (b) where $R^1$-$R^5$ are as defined in the Summary of the Invention provides a compound of Formula (I). The reaction is carried out in a suitable organic solvent, including but not limited to, diethyl ether, tetrahydrofuran, acetonitrile, benzene, toluene, xylene, and the like, or mixtures thereof and optionally in the presence of an organic or inorganic base. Preferably, the organic base is triethylamine, pyridine, N-methylmorpholine, collidine, diisopropylethylamine, and the like. Preferably, the inorganic base is cesium carbonate, sodium carbonate, sodium bicarbonate, and the like. The reaction is optionally carried out in the presence of a drying agent such as molecular sieves. The reaction can be carried out at about −78° C. to about 150° C., preferably at room temperature.

Compounds of formula (a) can be prepared by methods well known in the art. For example, a compound of formula (a) where $R^6$ is phenyl or 4-fluorophenyl, $R^7$ is trifluoromethyl, and $R^8$ is hydrogen can be readily prepared from commercially available 2,2,2-trifluoroacetophenone or 2,2,4'-tetrafluoroacetophenone respectively, by reducing the keto group to an alcoholic group with a suitable reducing agent such as sodium borohydride, lithium aluminum hydride, and the like. The solvent used depends on the type of reducing agent. For example, when sodium borohydride is used the reaction is carried out in an alcoholic organic solvent such as methanol, ethanol, and the like. When lithium aluminum hydride is used the reaction is carried out in an ethereal solvent such as tetrahydrofuran, and the like. Reaction of 2,2,2-trifluoro-1-phenylethanol or 2,2,2-trifluoro-1-(4-fluorophenyl)ethanol with triflic anhydride or methanesulfonyl chloride provides the desired compound (a). Optically enriched compound of formula (a) can be obtained by reduction of the corresponding halogenated acetophenone with a suitable reducing agent such as catecholborane or BH$_3$-DMS complex in the presence of a suitable catalyst such as (S) or (R)-CBS catalyst or (R) or (S)-α,α-diphenyl-2-pyrrolidine-methanol in the presence of BBN to provide chiral alcohol which is then converted to compound (a) as described above. Compounds of formula (b) can be prepared by methods well known in the art. Some such methods are described in PCT Applications Publication Nos. WO 03/075836 and 03/029200 and U.S. Pat. No. 6,353,017 the disclosures of which is are incorporated herein by reference in their entirety.

Alternatively, a compound of Formula (I) can be prepared by reacting a compound of formula (a) with a compound of formula (b') under the reaction conditions described above to provide a compound of formula (Ia) which upon dehydration of the amido group using suitable dehydrating agents such as POCl$_3$, trifluoroacetic anhydride, cyanuric chloride, and the like, provides a compound of Formula (I).

Alternatively, a compound of Formula (I) can be prepared as illustrated and described in Method (B) below.

Method (B)

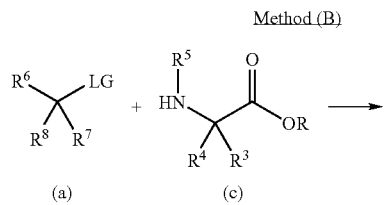

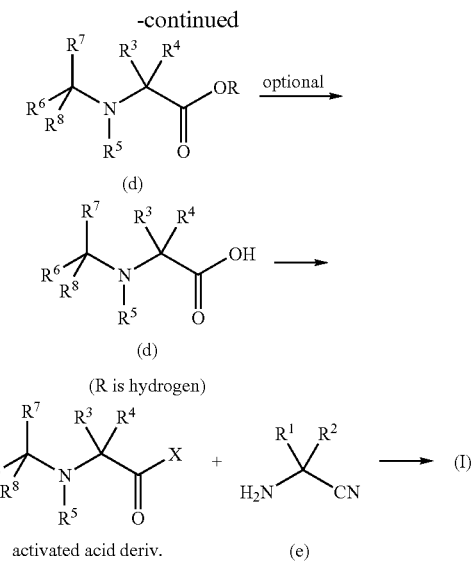

activated acid deriv. (e)

Reaction of a compound of formula (a) where LG is a suitable leaving group such as trifluoromethansulfonate, and the like, and $R^6$, $R^7$, and $R^8$ are as defined in Summary of the Invention with a compound of formula (c) where $R^3$-$R^5$ are as defined in the Summary of the Invention and R is hydrogen or a suitable carboxy protecting group such as alkyl, and the like, under the reaction conditions described in Method (A) above, provides a compound of formula (d). Other suitable carboxy protecting groups and reaction conditions for putting them on and removing them can be found in Greene, T. W.; and Wuts, P. G. M.; *Protecting Groups in Organic Synthesis*; John Wiley & Sons, Inc. 1999, the disclosure of which is incorporated herein by reference in its entirety.

Compounds of formula (c) are either commercially available or they can be prepared by methods well known in the art. For example, alanine, cysteine, aspartic acid, glutamic acid, phenylalanine, histidine, and lysine are commercially available. Others can be prepared by methods well known in the art. Some such methods are described in PCT Applications Publication Nos. WO 03/075836, WO 00/55144, WO 01/19816, WO 02/20485, WO 03/029200, U.S. Provisional Application No. 60/422,337, U.S. Pat. Nos. 6,353,017B1, 6,492,662B1, 353,017 B1 and 6,525,036B1, 6,229,011B1, 6,610,700, the disclosures of which are incorporated herein by reference in their entirety.

Removal of the carboxy protecting group, provides a compound of formula (d) where R is hydrogen which is then converted to an activated acid derivative (X is a leaving group) which upon reaction with an aminoacetonitrile compound of formula (e) provides a compound of Formula (I). The conditions used to remove the carboxy protecting group depend on the nature of the carboxy protecting group. For example, if R' is alkyl, it is removed under basic hydrolysis reaction conditions utilizing aqueous base such as aqueous lithium hydroxide, sodium hydroxide, and the like in an alcoholic solvent such as methanol, ethanol, and the like.

The activated acid derivative can be prepared and then reacted with compound (e) in a stepwise manner or the acid derivative can be generated in situ in the presence of compound (e). For example, if the activated acid is acid halide it is first prepared by reacting (d) with a halogenating agent such as thionyl chloride, oxalyl, chloride and the like and then reacted with compound (e). Alternatively, the activated acid derivative is generated in situ by reacting compound (d) and (e) in the presence of a suitable coupling agent e.g., benzotriazole-1-yloxy-trispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyluronium hexafluorophosphate (HATU), 1-(3-dimethylaminopropyl)-3-ethylcarbodiimide hydrochloride (EDC), 1,3-dicyclohexyl-carbodiimide (DCC), an the like, optionally in the presence of 1-hydroxybenzotriazole (HOBT), and in the presence of a base such as N,N-diisopropylethylamine, triethylamine, N-methylmorpholine, and the like. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like. Alternatively, the activated acid can be reacted with $CR^1R^2(NH_2)CONH_2$ where $R^1$ and $R^2$ are as described in the Summary of the Invention, followed by conversion of the —$CONH_2$ group to the cyano group as described above.

Alternatively, a compound of Formula (I) can be prepared as illustrated and described in Method (C) below.

described in PCT Application Publication No. WO 03/075836, the disclosure of which is incorporated herein by reference in its entirety.

Compound (g) where R' is a hydroxy protecting group is then converted to a corresponding compound of formula (g) where R' is hydrogen by removal of the hydroxyl protecting group. Suitable reaction conditions for removing hydroxy protecting group can be found in Greene, T. W.; and Wuts, P. G. M.; *Protecting Groups in Organic Synthesis*; John Wiley & Sons, Inc. 1999.

Compound (g) where R' is hydrogen is then converted to a compound of formula (h) utilizing suitable oxidizing agent such as Jones oxidizing reagent, $H_5IO_6/CrO_3$, and the like. Compound (h) is then converted to a compound of Formula (I) as described above.

Alternatively, a compound of Formula (I) where $R^4$ is -alkylene-$S(O)_{n3}$—$R^{22}$ where n3 is 0-2 and $R^{22}$ is alkyl, aralkyl, cycloalkylalkyl, heteroaralkyl, or hetereocyclylalkyl can be prepared as illustrated and described in Method D below.

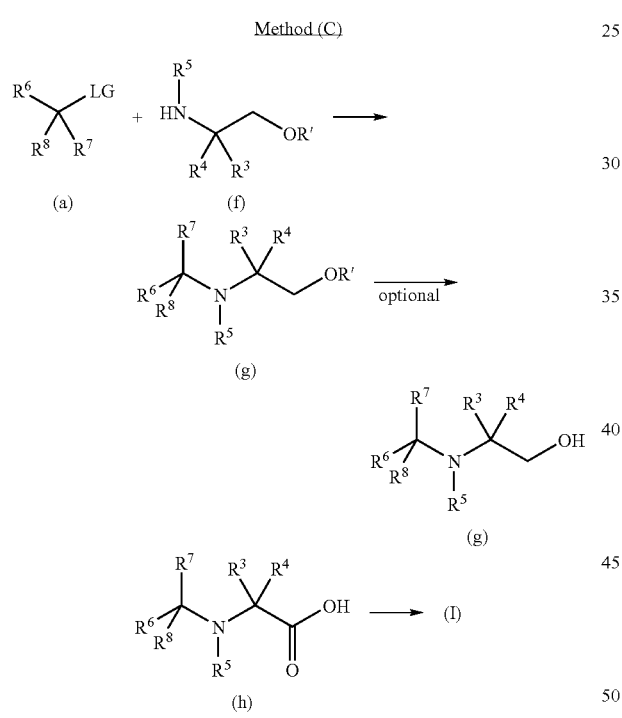

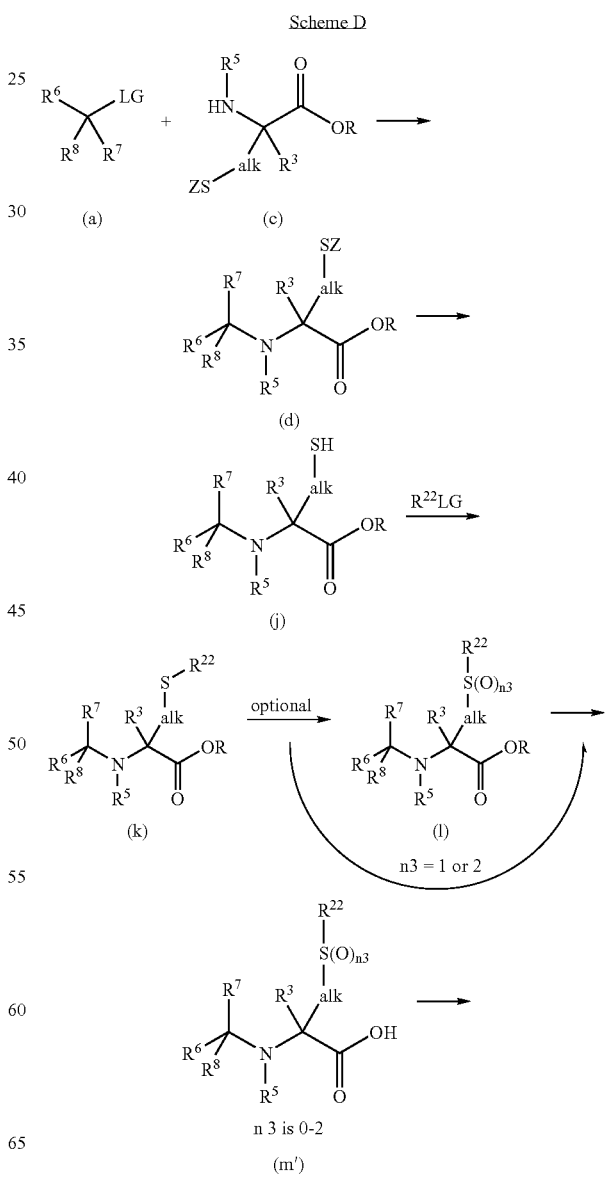

Reaction of a compound of formula (a) where LG is a suitable leaving group such as trifluoromethansulfonate, and the like, and $R^6$, $R^7$, and $R^8$ are as defined in Summary of the Invention with a compound of formula (f) where $R^3$-$R^8$ are as defined in the Summary of the Invention and R' is a suitable hydroxylprotecting group such as alkyl, and the like, under the reaction conditions described in Method (A) above, provides a compound of formula (g). Suitable amino acid protecting groups and reaction conditions for putting them on and removing them can be found in Greene, T. W.; and Wuts, P. G. M.; *Protecting Groups in Organic Synthesis*; John Wiley & Sons, Inc. 1999.

Compounds of formula (g) can be prepared from corresponding natural and unnatural acids of formula (c) by methods well known in the art. Some such procedures are

43

-continued

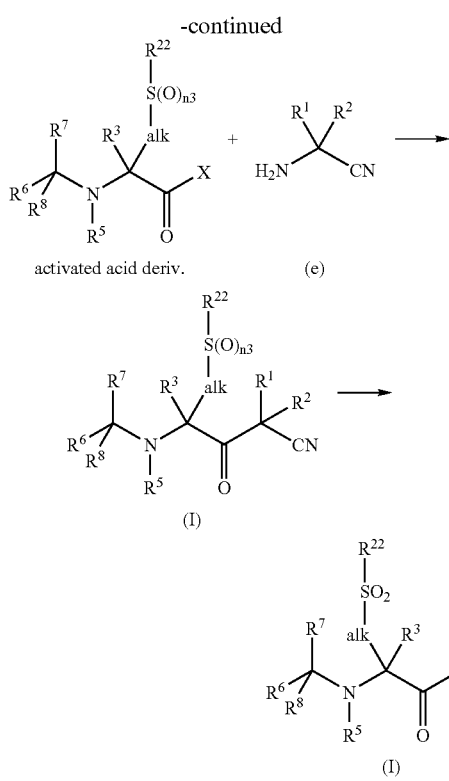

activated acid deriv. (e)

In Method (D), a compound of formula (a) is reacted with a compound of formula (c) where R is hydrogen or a carboxy protecting group, $R^3$ and $R^5$ are as defined in the Summary of the Invention, and $R^4$ is -(alkylene)-SZ where Z is a suitable thiol protecting group such as trityl, diphenylmethyl, and the like, under reaction conditions described above to provide a compound of formula (d). Removal of the thiol protecting group provides a compound of formula (j). Again, the deprotecting conditions depend on the nature of the thiol protecting group. A list of suitable thio protecting groups, reaction conditions for putting them on and removing them can be found in Greene, T. W.; and Wuts, P. G. M.; *Protecting Groups in Organic Synthesis*; John Wiley & Sons, Inc. 1999, the disclosure of which is incorporated herein by reference in its entirety.

Reaction of a compound of formula (j) with an alkylating agent of the formula $R^{22}LG$ where $R^{22}$ is alkyl, cycloalkylalkyl, heterocyclylalkyl, aralkyl or heteroaralkyl and LG is a leaving group such as halo, tosylate, mesylate, triflate, and the like, and in the presence of a base under conditions well known in the art provides a compound of formula (k). The sulfur atom in compound (k) can be optionally oxidized to sulfoxide or sulfone with a suitable oxidizing agent such as OXONE®, and the like to provide a compound of formula (l). Removal of the carboxy protecting group from compound (k) or (l) provides a compound of formula (m') which is then converted to an activated acid derivative and reacted with 2-aminoacetonitrile compound of formula (e) to provide a compound of Formula (I) as described above. A compound of Formula (I) where n3 is 0 can be converted to a corresponding compound of Formula (I) where n3 is 1 or 2 under the oxidation reaction conditions described above.

44

Alternatively, the above compounds of Formula (I) can be prepared by first reacting a compound of formula (c) where R is hydrogen with a compound of formula (e) to provide a compound of formula (n'):

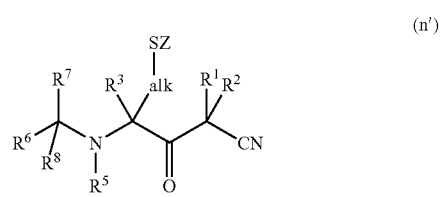

Compound (n') is then converted to a compound of Formula (I) by removing the thiol protecting group and reacting the resulting compound with a compound of formula $R^{22}LG$, followed by optional oxidation of the sulfur atom to sulfone as described above.

Alternatively, the activated acid can be reacted with $CR^1R^2$ $(NH_2)CONH_2$ where $R^1$ and $R^2$ are as described in the Summary of the Invention, followed by conversion of the —$CONH_2$ group to the cyano group by methods well known in the art. The sulfur atom in compound (I) can be optionally oxidized to sulfoxide or sulfone with a suitable oxidizing agent such as OXONE®, and the like to give a corresponding compound of Formula (I) where n3 is 1 or 2.

Similarly, other compounds of Formula (I) where $R^z$ is $R^4$ where $R^4$ is -(alkylene)-$X^1$—$R^{22}$ where $X^1$ is —$NR^{23}$—, —O—, $S(O)_{n3}$—, —CO—, —COO—, —OCO—, —$NR^{23}CO$—, —$CONR^{23}$—, —$NR^{23}SO_2$—, —$SO_2NR^{23}$—, —$NR^{23}COO$—, —$OCOONR^{23}$—, —$NR^{23}CONR^{24}$—, or —$NR^{23}SO_2NR^{24}$— where $R^{22}$, $R^{23}$ and $R^{24}$ are as defined in the Summary of the Invention can be prepared from commercially available starting materials such as lysine, glutamic acid, aspartic acid, serine, and homoserine as described above or by methods well known in the art. Some such methods are described in U.S. Pat. No. 6,136,844 the disclosure of which is incorporated herein by reference in its entirety.

EXAMPLES

The present invention is further exemplified, but not limited by, the following examples that illustrate the preparation of compounds of Formula (I) (Examples) and intermediates (References) according to the invention.

Example A

Synthesis of 2(RS)-benzyloxycarbonylamino-4(RS)-(2-methoxyphenyl)pentanoic acid

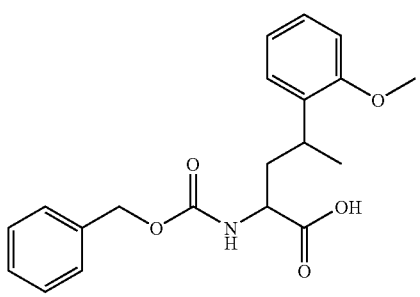

To d,l-2-methoxy-α-methylbenzyl alcohol (0.5 g, 3.29 mmol) was added 48% aq. HBr (2 mL) and the reaction mixture was stirred rapidly for 1.5 h. The reaction mixture was diluted with hexane (30 mL), washed with water, dried with MgSO$_4$, filtered, and evaporated under vacuum. The crude d,l-2-methoxy-α-methylbenzyl bromide was added to a solution of tributyltin hydride (0.67 mL, 2.49 mmol), Z-dehydroalanine methyl ester (0.25 g, 1.06 mmol), and 2,2'-azobisisobutyronitrile (15 mg, 0.09 mmol) in benzene (5 mL). The reaction mixture was heated at 80° C. under a nitrogen atmosphere for 5 h. Benzene was removed under vacuum and the residue was dissolved in methanol (20 mL). 2N KOH (5 mL) was added and the mixture was rapidly stirred at room temperature over night. Methanol was removed under vacuum and the residue was diluted with water (20 mL). The aqueous solution was washed with ether to remove the tin by products. The aqueous layer was acidified with 6 N HCl (aq.) and the product was extracted with ethyl acetate. The combined organic layers were washed with brine, dried with MgSO$_4$, filtered, and evaporated under vacuum to give 2-benzyloxy-carbonylamino-4-(2-methoxyphenyl)pentanoic acid (190 mg, 0.53 mmol) as a mixture of diastereomers in sufficiently pure form to be used without further purification. MS: (M$^+$+H) 358, (M$^+$–H) 356.

Following the procedure described above, and utilizing appropriate starting materials the following amino acids were prepared:
2-benzyloxy-carbonylamino-4-(2-methoxyphenyl)hexanoic acid;
2-benzyloxy-carbonylamino-4-(4-fluorophenyl)pentanoic acid;
2-benzyloxy-carbonylamino-4-(4-chlorophenyl)pentanoic acid;
2-benzyloxy-carbonylamino-4-(4-methoxyphenyl)pentanoic acid;
2-benzyloxy-carbonylamino-4-(2-trifluoromethylphenyl)pentanoic acid;
2-benzyloxy-carbonylamino-4-(3-trifluoromethylphenyl)pentanoic acid;
2-benzyloxy-carbonylamino-4-(napth-1-yl)pentanoic acid;
2-benzyloxy-carbonylamino-4-(2,6-dimethylphenyl)pentanoic acid;
2-benzyloxy-carbonylamino-4-(2,4-difluorophenyl)pentanoic acid;
2-benzyloxy-carbonylamino-4-(2,4-dimethylphenyl)pentanoic acid;
2-benzyloxy-carbonylamino-4-(2,5-dimethylphenyl)pentanoic acid; and
2-benzyloxy-carbonylamino-4-(2,4-dichlorophenyl)pentanoic acid.

The benzyloxycarbonyl group can be removed as described in Example B below to give the corresponding free amino acid.

Example B

Synthesis of 2(S)-2,6-difluorophenylalanine

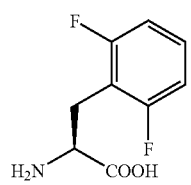

Step 1

N-(Benzyloxycarbonyl)-α-phosphonoglycine trimethyl ester (Aldrich No. 37, 635-3; 6.7 g, 20 mmol) and 1,8-diazabicyclo[5,4,0]undec-7-ene (Aldrich No. 13, 900-9; 3.3 mL, 22 mmol) were dissolved in methylene chloride (11 mL) and stirred at room temperature for 15 min, and then cooled to <–30° C. A solution of 2,6-difluorobenzaldehyde (1.9 mL, 20 mmol) in methylene chloride (25 mL) was added to the reaction mixture dropwise over 20 min. The reaction mixture was stirred for another 20 min, and then allowed to warm up to room temperature for 30 min. The reaction mixture was then poured into ethyl ether (300 mL) and washed with 1 N HCl, brine and dried over MgSO$_4$. Rotary evaporation gave crude 2-benzyloxycarbonylamino-3-(2,6-difluorophenyl)acrylic acid methyl ester which was purified by chromatography on a Medium Pressure Liquid Column (MPLC) eluting with 20% ethyl acetate/80% hexane to give pure product (5 g, 72% yield, liquid).

Step 2

A mixture of 2-benzyloxycarbonylamino-3-(2,6-difluorophenyl)acrylic acid methyl ester (14.4 mmol), and catalyst, (+)-1,2-bis-[(2S,5S)2,5-diethylphopholano]benzene (cyclooctadiene)rhodium (1) trifluoromethanesulfonate (Strem. Chemical No. 45-0151; 104 mg, 0.14 mmol) was dissolved in ethanol (150 mL). Hydrogenation was performed at 50 psi H$_2$ at room temperature over 2 days. The solvent was then removed by rotary evaporation to give 2(S)-benzyloxycarbonylamino-3-(2,6-difluorophenyl)propionic acid methyl ester.

Step 3

2(S)-Benzyloxycarbonylamino-3-(2,6-difluorophenyl)propionic acid methyl ester (5 g, 14.4 mmol) was dissolved in methanol (60 mL) and cooled on ice. 1 N NaOH (22 mL, 22 mmol) was added dropwise over 15 min. The reaction mixture was removed from cooling bath and stirring was continued at room temperature for 4 h. The solvent was then removed by rotary evaporation and the residue was treated with water (100 mL) and then with 1 N HCl to adjust the pH to 4. The product was extracted with ethyl acetate (300 mL, 200 mL). Evaporation of the solvent and crystallization of the residue from methylene chloride/hexane gave 2(S)-benzyloxycarbonylamino-3-(2,6-difluorophenyl)propionic acid (4.6 g, 13.7 mmol, 94% yield).

Step 4

2(S)-Benzyloxycarbonylamino-3-(2,6-difluorophenyl)propionic acid was hydrogenated at 50 psi in ethanol (25 mL) in the presence of 5% palladium on activated carbon (600 mg) for 24 h. The catalyst was removed by filtration through Celite® and the solvent evaporated to give a residue which was crystallized from ethyl ether to give 2(S)-2,6-difluorophenylalanine (2.2 g, 11 mmol, 80% yield). $^1$H NMR (DMSO-d$_6$): δ 7.28 (m, 1H), 7.0 (t, J=7.6 Hz, 2H), 2.77 (m, 2H). MS: 202.2 (M+1), 199.7 (M–1).

Example C

Synthesis of 2(RS)-amino-4-methyl-4-phenylpentanoic acid

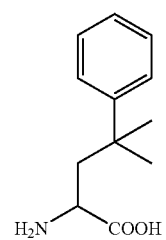

Step 1

4-Methyl-4-phenyl-1-pentene was prepared by reacting 2-phenyl-2-propanol with 3-(trimethylsilyl)propene by the method of Cella, *J. Org. Chem.*, 1982, 47, 2125-2130.

Step 2

4-Methyl-4-phenyl-1-pentene was ozonolyzed at −78° C. in dichloromethane followed by dimethyl sulfide quenching to give crude product which was purified by silica gel chromatography to give 3-methyl-3-phenylbutanal which was then converted to the title compound by proceeding as described in PCT application publication No. WO 2004/052921, Reference C, on page 68 of the application.

Example D

Synthesis of 2(S)-benzyloxycarbonylamino-3-pyrazol-1-ylpropionic acid

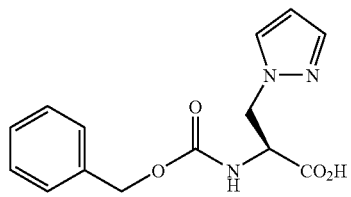

The title compound was prepared by treating S-benzyloxycarbonylserine-β-lactone with pyrazole in acetonitrile at 60° C. for 16 h (see *J. Am. Chem. Soc.*, 1985, 107, 7105-7109).

Following the procedure described above, but substituting pyrazole with 1,2,4-triazole and 1,2,3-triazole provided 2(S)-benzyloxycarbonylamino-3-[1,2,4]-triazol-1-ylpropionic acid and 2(S)-benzyloxycarbonylamino-3-[1,2,3]-triazol-1-ylpropionic acid respectively.

Example E

Synthesis of 2(S)-(tert-butoxycarbonyl)amino-3-thiazol-2-ylpropionic acid

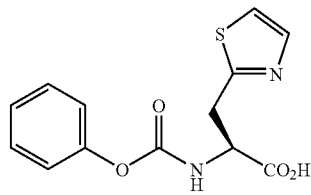

To 2-tert-butoxycarbonylamino-3-thiazol-2-ylpropionic acid methyl ester (500 mg, 1.75 mmol) in a mixture of acetonitrile (6 mL) and 0.2 M aqueous NaHCO₃ (12 mL) was added Alcalase (2.4 L, 0.08 mL), and the solution was stirred vigorously at room temperature for about 2.5 h. The reaction mixture was then evaporated at 30° C. to remove acetonitrile, and the aqueous residue was washed with ether. The aqueous phase was acidified with 6 N HCl to pH 3 and the solution was extracted with ethyl acetate. The combined organic layers were then dried and evaporated to yield 2(S)-tert-butoxycarbonylamino-3-thiazol-2-ylpropionic acid (204 mg).

Reference F

Synthesis of 4-amino-4-cyano-1-ethylpiperidine

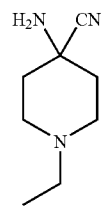

A mixture of 1-ethyl-4-piperidone (13.2 mL, 100 mmol), ammonium chloride (21.4 g, 400 mmol), sodium cyanide (19.6 g, 400 mmol) and water (550 mL) was stirred at room temperature for 48 h. The pH of the reaction mixture was adjusted to 10.1 and the product was extracted with ethyl acetate. The organic extracts were washed with brine and dried over magnesium sulfate. Rotary evaporation of the solvent gave a mixture of 4-amino-4-cyano-1-ethylpiperidine and 4-hydroxy-4-cyano-1-ethylpiperidine (7.67 g). This mixture of products was treated with 7M ammonia in methanol (20 mL) and allowed to stand at room temperature for 24 h. The methanol and excess ammonia were removed in vacuo and the residue was cooled to give 4-amino-4-cyano-1-ethylpiperidine as a crystalline solid (7.762 g).

Reference G

Synthesis of 2(S)-benzyloxycarbonylamino-3-(1-methylcyclopentyl)-propionic acid

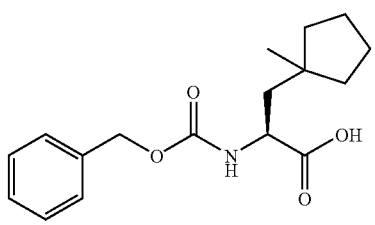

Step 1

1-Methylcyclopentanol (20 g, 0.2 mol) was added to hydrobromic acid (40 mL) at room temperature. After stirring for 1 h, the solution was extracted with hexane and the hexane was washed with brine and dried with magnesium sulfate. After concentration of the organic layer, 20.5 g of 1-methylcyclopentyl bromide was obtained.

Step 2

Tributyltin hydride (37.8 g, 130 mmol) was added at reflux to a 500 mL of flask charged with benzene (200 mL) was added Z-dehydro-Ala-OH (15 g, 64 mmol), 1-methylcyclopentanyl-bromide (20.5 g) and AIBN (1.9 g). After 2 h, the solvent was removed and the residue was purified by column chromatograph to yield 2-benzyloxycarbonylamino-3-(1-methyl-cyclopentyl)-propionic acid methyl ester (7.9 g).

Step 3

2-Benzyloxycarbonylamino-3-(1-methylcyclopentyl)-propionic acid methyl ester (7.6 g, 23.8 mmol) was dissolved in a mixture of acetonitrile (82 mL) and 0.2 M aqueous NaHCO₃ (158 mL) and Alcalase 2.4 L (1.1 mL) was added and the reaction mixture was stirred vigorously for 8 h. The reaction mixture was then evaporated at 30° C. to remove acetonitrile, and the aqueous residue was washed with ether. The ethereal layer was concentrated to yield (R)-2-benzyloxycarbonyl-amino-3-(1-methylcyclopentyl)propionic acid methyl ester (1.9 g). The aqueous phase was filtered with Celite®, the pH was adjusted to 3 with 6N HCl, and the solution was extracted with ethylacetate. The ethyl acetate layer was dried and evaporated to yield 2(S)-benzyloxycarbonylamino-3-(1-methylcyclopentyl)-propionic acid (1.4 g).

Reference H

Synthesis of trifluoromethanesulfonic acid 2,2,2-trifluoro-1-(4-fluorophenyl)ethyl ester

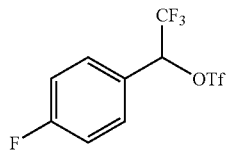

Step 1

To a stirred solution of 2,2,2,4'-tetrafluoroacetophone (10 g, 52.1 mmol) in methanol (50 mL) was added NaBH₄ (0.98 g, 26.5 mmol) at 0° C. After stirring at 25° C. for 2 h, the reaction mixture was quenched by adding 1N HCl (100 mL) and then extracted with ethyl ether. The ether extract was washed with brine, dried with MgSO₄, and concentrated to give 2,2,2-trifluoro-1-(4-fluorophenyl)ethanol (11.32 g) which was used in next step without further purificaiton.

Step 2

NaH (640 mg, 16 mmol, 60% in mineral oil) was washed twice with hexane (20 mL) and then suspended in dried diethyl ether (20 mL). A solution of 2,2,2-trifluoro-1-(4-fluoro-phenyl)ethanol (1.94 g, 10 mmol) in diethyl ether (10 mL) was added at 0° C. After stirring for 2 h at room temperature, a solution of trifluoromethanesulfonyl chloride (1.68 g, 10 mmol) in diethyl ether (10 mL) was added. After 2 h, the reaction mixture was quenched by adding a solution of NaHCO₃ and the product was extracted with diethyl ether. The extracts were washed with brine and dried, and the solvent was removed to yield trifluoromethanesulfonic acid 2,2,2-trifluoro-1-(4-fluorophenyl)ethyl ester (3.3 g).

Proceeding as described in Example H above, trifluoromethanesulfonic acid 2,2,2-trifluoro-1-phenylethyl ester was prepared.

Reference I

Synthesis of 2,2,2-trifluoro-1R-(4-fluorophenyl)ethanol

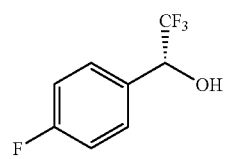

To a −78° C. toluene (25 mL)/dichloromethane (25 mL) solution of 2,2,2,4'-tetrafluoroacetophenone (2.5 g, 13.01 mmol) and 1M S-CBS catalyst (1.3 mL, 1.3 mmol) was added freshly distilled catecholborane (1.66 mL, 15.62 mmol). The reaction mixture was maintained at −78° C. for 16 h at which time 4N HCl (5 mL in dioxane) was added and the reaction mixture was allowed to warm to room temperature. The reaction mixture was diluted with ethyl acetate and washed with a saturated brine solution. The organic layer was dried over magnesium sulfate, filtered and concentrated to provide a solid. The solid was suspended in hexanes and filtered off. The hexanes filtrate containing the desired product was concentrated and the residue subjected to flash chromatography (10 hexanes: 1 ethylacetate) to provide the title compound as colorless oil (2.2 g, 87% yield). The ratio of enantiomers was determined to be 95:5 by chiral BIPLC (Chiralcel OD column, 95 hexanes: 5 isopropanol mobile phase. Ret. time major product 6.757 min. Ret. time minor isomer 8.274 min.).

Reference J

Synthesis of 2(R)-3-cyclopropylmethylsulfanyl-2-(2,2,2-trifluoro-1 (RS)-phenyl-ethylamino)propan-1-ol

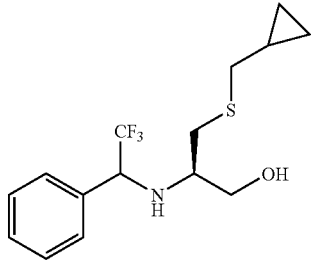

Step 1

An ice water bath cooled solution of L-cysteine in 1N sodium hydroxide (740 mL) and dioxane (740 mL) was treated with bromomethylcyclopropane (50 g, 370 mmol). The reaction mixture was allowed to warm to room temperature and stirred for 16 h. Dioxane was removed under reduced pressure and the resulting aqueous solution was adjusted to pH 6 with 6N HCl and placed in a refrigerator for 20 h. The product was collected by vacuum filtration, washed with hexanes and lyophilized to give 2(R)-amino-3-cyclopropylmethyl-sulfanylpropionic acid (57.28 g) as a white solid.

Step 2

To an ice water cooled solution of lithium aluminum hydride (200 mL of 1.0 M) was added solid 2(R)-amino-3-cyclopropylmethylsulfanylpropionic acid. The addition was done by tapping in portions through a funnel in such a manner as to control hydrogen gas evolution. The ice bath was removed, and the reaction mixture was heated at reflux for 16 h. The reaction mixture was removed from heat and cooled in an ice water bath. Diethyl ether (110 mL) was added, followed by dropwise addition of water (5 mL), 15% aqueous sodium hydroxide (5 mL), and water (15 mL). After stirring in the ice water bath for 1.5 h, the reaction mixture was filtered. The filtrate was dried over anhydrous sodium sulfate, and concentrated to give 2(R)-amino-3-cyclopropylmethylsulfanylpropan-1-ol (14.9 g).

Step 3

To a stirred solution of 2(R)-amino-3-cyclopropylmethyl-sulfanylpropan-1-ol (80.5 mg, 0.5 mmol) in anhydrous THF (3 mL) were added activated 4 Å molecular sieves (250 mg) and N-methylmorpholine (51 mg, 0.5 mmol). After stirring for 10 min, trifluoromethanesulfonic acid 2,2,2-trifluoro-1-phenylethyl ester (190.5 mg, 0.5 mmol) was added and the reaction was stirred at room temperature for 2 days. The reaction mixture was filtered and the filtrate was concentrated. The residue was purified by flash column chromatography to afford the desired mixture of diastereomers of 2(R)-3-cyclopropylmethyl-sulfanyl-2-(2,2,2-trifluoro-1(RS)-phenylethylamino)propan-1-ol. LC-MS: 318.3(M-1), 320.8 (M+1).

Reference K

Synthesis of 1-aminocyclopropanecarbonitrile hydrochloride

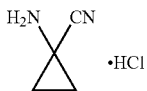

Step 1

A mixture of benzophenone imine (25 g, 0.138 mol, Aldrich) and aminoacetonitrile hydrochloride (25 g, 0.270 mol, Lancaster) in dichloromethane (1000 mL) was stirred in a 2 L Erlenmeyer flask under nitrogen at room temperature for 5 days. The reaction mixture was filtered to remove the precipitated ammonium chloride and the filtrate was evaporated to dryness in vacuo. The resulting residue was dissolved in ether (400 mL) washed with water (200 mL) and brine. After drying over magnesium sulfate the solution was evaporated to give (benzhydrylideneamino)acetonitrile (47.89 g).

Step 2

A solution of sodium hydroxide (91 g, 2.275 mol) in water (91 mL) in a 2L flask was cooled on ice under nitrogen and then treated with benzyl triethyl ammonium chloride (2.0 g, 0.0088 mol, Aldrich) and (benzhydrylideneamino)acetonitrile (47.89 g) in toluene (100 mL). 1,2-Dibromoethane (23 mL, 122.4 mmol, Aldrich) was then added dropwise over 25 min, to the reaction mixture with mechanical stirring and cooling to maintain the internal temperature near +10° C. The reaction mixture was then stirred vigorously for 24 h at room temperature and then poured into ice water and extracted with toluene. The combined extracts were washed with brine and then treated with MgSO$_4$ and Norite. After filtering, toluene was removed by rotary evaporation to give an oil (67 g). The residue was dissolved in boiling hexane (400 mL), treated with Norite and filtered hot and allowed to cool. A dark oil separated and which was removed by pipet (~2 mL). Scratching induced crystallization in the remaining solution which was cooled on ice for 2 h. Light yellow crystals were collected by filtration and washed with cold hexane to give 1-(benzhydrylideneamino)cyclopropane-carbonitrile (30.56 g).

Step 3

A mixture of 1-(benzhydrylideneamino)cyclopropanecarbonitrile (30.56 g, 0.124 mol) in concentrated HCl (12 mL) in water (100 mL) and ether (100 mL) was stirred at room temperature for 15 h. The ether layer was discarded and the aqueous layer was washed with ether. The aqueous layer was then freeze dried to give the title compound as a tan powder (13.51 g).

Reference L

Synthesis of 2(R)-amino-3-[2-(difluoromethoxy)phenylmethanesulfanyl]propionic acid

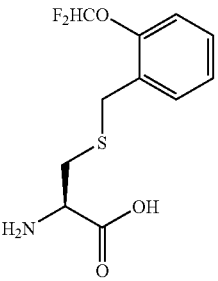

A solution of L-cysteine (5.1 g, 42.2 mmol) in 2N NaOH (42.2 mL) was cooled in an ice water bath. Neat 1-bromomethyl-2-difluoromethoxybenzene (10 g, 42.2 mmol) was added and the reaction mixture was allowed to stir and warm to room temperature over 4 h. The reaction mixture was cooled in an ice bath and the pH was adjusted 6 using 3N HCl, then 1N HCl when the white precipitate that formed became too thick to allow stirring. The precipitates were collected by vacuum filtration, washed with hexanes and dried by lyophilization to give the title compound (11.14 g) as a white solid.

Reference M

Synthesis of 4-amino-1-(2,2,2-trifluoroethyl)piperidine-4-carbonitrile hydrochloride

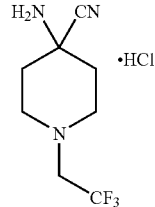

Step 1

In a solution of 1,4-dioxa-8-aza-spiro[4.5]decane (14.3 g, 100 mmol) in CH$_2$Cl$_2$ (200 mL) was added Et$_3$N (15.2 g, 150 mmol), DMAP (30 mg) and trifloroacetic acid anhydride (25.2 g, 150 mmol) at 0° C., then allowed to warm-up to room temperature and stirred for 12 h. The reaction mixture was quenched with water and washed with 1N HCl and brine, dried with MgSO$_4$. Removal of the solvent, yielded 1-(1,4-dioxa-8-aza-spiro[4.5]dec-8-yl)-2,2,2-trifluoroethanone (35 g). The crude product was used in the next reaction.

Step 2

In the solution of 1-(1,4-dioxa-8-aza-spiro[4.5]dec-8-yl)-2,2,2-trifluoroethanone (20 g, 83.7 mmol) in THF, borane-methyl sulfide complex (83.7 mL, 2M solution in THF) was added at 0° C. After refluxing the reaction mixture for 12 h, the reaction was cooled and quenched with MeOH. After removal of THF, the residue was extracted with ethyl acetate and washed with brine, dried with MgSO$_4$ and concentrated to give 8-(2,2,2-trifluoroethyl)-1,4-dioxa-8-aza-spiro[4.5]decane (19 g) was obtained.

Step 3

8-(2,2,2-Trifluoroethyl)-1,4-dioxa-8-aza-spiro[4.5]decane (3.7 g, 16 mmol) was added to a solution of 5% HCl (45 mL) and acetone (8 mL). After refluxing for 12 h, the solvent was removed to give crude 1-(2,2,2-trifluoroethyl)piperidin-4-one hydrochloride which was used in the next reaction.

Step 4

A solution of ammonium chloride (3.2 g, 60 mmol) and potassium cyanide (2.94 g, 60 mmol) was prepared in water (25 mL) and 1-(2,2,2-trifluoroethyl)-piperidin-4-one hydrochloride (3.5 g, 15 mmol) was added and the reaction mixture was stirred for 2 days. The solution was then brought to pH 11 with sodium carbonate and the reaction mixture was extracted with ethyl acetate. After drying over Na$_2$SO$_4$, the solvent was removed to yield a mixture of 4-hydroxy-1-(2,2,2-trifluoroethyl)piperidine-4-carbonitrile and 4-amino-1-(2,2,2-trifluoroethyl)piperidine-4-carbonitrile. This mixture was then treated with 7N ammonia solution in MeOH for 12 h at room temperature. After removal of the solvent, the residue was dissolved in ethyl ether and treated with 4N HCl solution in dioxane. The solids were filtered and dried under vacuum, to yield 4-amino-1-(2,2,2-trifluoroethyl)piperidine-4-carbonitrile hydrochloride (2.5 g).

Proceeding as described in Reference M, Steps 1-3 above, 1-ethylpiperidin-4-one hydrochloride was prepared.

Example 1

Synthesis of 2R—N-(1-cyanocyclopropyl)-3-(pyridin-2-ylmethylsulfanyl)-2-(2,2,2-trifluoro-1RS-phenylethylamino)propionamide (Method A)

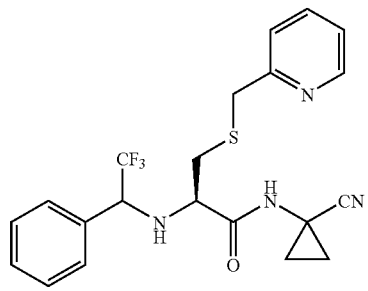

Step 1

To a solution of (Boc-Cys-OH)$_2$ (20 g, 45.4 mmol) and P(CH$_2$CH$_2$COOH)$_3$·HCl (15.61 g, 54.47 mmol) in DMF (162 mL) was added 5N KOH (109 mL) slowly over 20 min. After stirring overnight, 2-picolylchloride hydrochloride (22.34 g, 136.2 mmol) was added in one portion and the reaction mixture was stirred at room temperature for 2.5 h. The pH of the solution was adjusted to 3 with 10N HCl and the product was extracted with methylene chloride. The combined organic extract was washed with sat. NaHCO$_3$, dried over MgSO$_4$, filtered and concentrated to give 2(R)—N-tert-butoxycarbonylamino-3-(pyridin-2-ylmethylsulfanyl)propionic acid which was crystallized from methylene chloride and hexane mixture to give pure product (13.70 g) as a white solid.

Step 2

2(R)-tert-Butoxycarbonylamino-3-(pyridin-2-ylmethylsulfanyl)propionic acid (1.644 g, 5.3 mmol) was dissolved in DMF, 1-aminocyclopropanecarbonitrile hydrochloride (747 mg, 6.3 mmol), HATU (2.4 g, 6.3 mmol) and N-methylmorpholine (2.3 mL, 21.2 mmol) were added and the reaction mixture was stirred at room temperature for 4 h. Saturated NaHCO$_3$ solution and ethyl acetate were added after stirring for 20 min at room temperature, aqueous layer was extracted by ethyl acetate. Combined organic layers was dried by MgSO$_4$ and removed under the reduced pressure. Purified by flash column (ethyl acetate) provided [1-(1-cyanocyclopropyl-carbamoyl)-2(R)-(pyridin-2-ylmethylsulfanyl)ethyl]carbamic acid tert-butyl ester (1.28 g).

Step 3

[1-(1-Cyanocyclopropylcarbamoyl)-2(R)-(pyridin-2-ylmethylsulfanyl)ethyl]carbamic acid tert-butyl ester (1.28 g, 3.4 mmol) was dissolved in THF, methanesulfonic acid (0.65 mL, 10 mmol) was added and the reaction mixture was stirred overnight at room temperature. Water (1 mL) and solid NaHCO$_3$ were added until no bubbles were observed. The product was extracted with ethyl acetate. The organic layer was dried with MgSO$_4$ and removed under the reduced pressure to get 2(R)-amino-N-(1-cyanocyclopropyl)-3-(pyridin-2-ylmethylsulfanyl)-propionamide as an oil (100% yield).

Step 4

To a stirred solution of 2(R)-amino-N-(1-cyanocyclopropyl)-3-(pyridin-2-ylmethyl-sulfanyl)propionamide (110 mg, 0.4 mmol) in anhydrous THF (2 mL) were added activated 4 Å molecular sieves (250 mg) and N-methylmorpholine (40 mg, 0.4 mmol). After 10 min, trifluoromethanesulfonic acid 2,2,2-trifluoro-1-phenylethyl ester (152 mg, 0.4 mmol) was added and the reaction mixture was stirred at room temperature for 2 days. The reaction mixture was filtered and the filtrate was concentrated and the residue was purified by flash column chromatography to afford a mixture of N-(1-cyanocyclopropyl)-3-(pyridin-2-ylmethylsulfanyl)-2(R)-(2,2,2-trifluoro-1(R)-phenylethylamino)propionamide and N-(1cyanocyclopropyl)-3-(pyridin-2-ylmethylsulfanyl)-2(R)-(2,2,2-trifluoro-1(S)-phenylethylamino)propionamide (65 mg). LC-MS: 433.3 (M−1), 435.1 (M+1), 457.1 (M+Na).

Example 2

Synthesis of (2S)-4-methyl-2-(2,2,2-trifluoro-1S-phenyl-ethylamino)-pentanoic acid methyl ester (Method B)

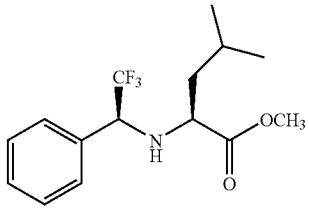

To a stirred solution of L-2-amino-4-methylpentanoic acid methyl ester HCl salt (181.5 mg, 1 mmol) in anhydrous THF (3 mL) were added activated 4 Å molecular sieves (500 mg) and N-methylmorpholine (202 mg, 2 mmol). After stirred for 10 min, R-trifluoro-methanesulfonic acid 2,2,2-trifluoro-1-phenylethyl ester (381 mg, 1 mmol) was added and the reaction was stirred at room temperature for 2 days. The reaction mixture then filtered and the filtrate was concentrated. The residue was purified by flash column chromatography to afford the desired (2S)-4-methyl-2-(2,2,2-trifluoro-1S-phenylethylamino)pentanoic acid methyl ester (185 mg).

Example 3

Synthesis of N-(1-cyanocyclopropyl)-3-(2-difluoromethoxyphenylmethanesulfonyl)-2(R)-[2,2,2-trifluoro-1 (s)-(4-fluorophenyl)ethylamino]propionamide (Method B)

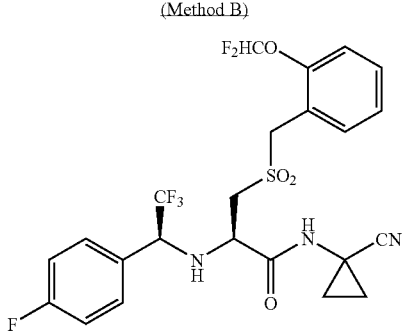

Step 1

A dried 50 mL of flask was charged sodium hydride, 60% dispersion in mineral oil (624 mg, 15.6 mmol) under $N_2$ and then washed with dried hexane (20 mL) twice. Dried ethyl ether (10 mL) was added and a solution of 2,2,2-trifluoro-1 (RS)-(4-fluorophenyl)ethanol (90% ee) (2.5 g, 12.89 mmol) in ethyl ether (10 mL) was added at 0° C. After completion of addition, the reaction mixture was allowed to warm up to room temperature and stirred for 1 h. A solution of trifluoromethanesulfonyl chloride (3.28 g, 19.5 mmol) in ethyl ether (10 mL) was added at 0° C. After completion of addition, the reaction was allowed to warm up to room temperature and stirred for 1 h. The solvent was removed under rot-vap and diluted with hexane (150 mL) and washed with a saturated $NaHCO_3$ n and brine. After drying with $MgSO_4$, the organic solvent was removed to give trifluor-methanesulfonic acid 2,2,2-trifluoro-1(RS)-(4-fluorophenyl)ethyl ester (3.15 g) (90% ee) as a colorless oil which was used in the next step without further purification.

Step 2

Into a stirred suspension of 2(R)-amino-3-(2-difluoromethoxyphenylmethanesulfanyl)-propionic acid (277 mg, 1 mmol) in DCM (3 mL) was added DIPEA (323 mg, 2.5 mmol) and trifluoromethanesulfonic acid 2,2,2-trifluoro-1 (RS)-(4-fluorophenyl)ethyl ester (489 mg, 1.5 mmol) (90% ee) at 25° C. After 12 h, HPLC showed diastereomeric mixture of two major products 3-(2-difluoromethoxyphenylmethanesulfanyl)-2(R)-[2,2,2-trifluoro-1(RS)-(4-fluorophenyl)ethylamino]-propionic acid and 1(RS)-(4-fluorophenyl)-2,2,2-trifluoroethane 3-(2-difluoromethoxyphenylmethanesulfanyl)-2(R)-[2,2,2-trifluoro-1(RS)-(4-fluorophenyl)-ethylamino]propionate (t=4.177, t=4.852). The reaction mixture was diluted with ethyl ether (150 mL) and washed with 1N HCl solution and brine. After drying with $MgSO_4$ the solvent was removed and the residue was purified by prep-HPLC to give 3-(2-difluoromethoxy-phenylmethanesulfanyl)-2(R)-[2,2,2-trifluoro-1(RS)-(4-fluorophenyl)ethylamino]propionic acid (178 mg) and 1(RS)-(4-fluorophenyl)-2,2,2-trifluoroethane 3-(2-difluoromethoxy-phenylmethanesulfanyl)-2(R)-[2,2,2-trifluoro-1 (RS)-(4-fluorophenyl)ethylamino]propionate (203 mg)

Step 3

To a solution of 1(RS)-(4-fluorophenyl)-2,2,2-trifluoroethane 3-(2-difluoromethoxy-phenylmethanesulfanyl)-2(R)-[2,2,2-trifluoro-1 (RS)-(4-fluorophenyl)ethylamino]propionate in THF (2 mL) and MeOH (1 mL) was added 1N solution of LiOH (1 mL) at 25° C. After 30 min, the solvent was removed and the residue was diluted with water (10 mL) and extracted with hexane to remove alcohol. The water phase was acidified by 1N HCl to pH=1-2 and extracted with ethyl ether (120 mL). After drying with $MgSO_4$, the solvent was removed under rot-vap, to give 3-(2-difluoromethoxy-phenylmethanesulfanyl)-2(R)-[2,2,2-trifluoro-1(RS)-(4-fluorophenyl)ethylamino]-propionic acid.

Step 4

In to a stirred solution of 3-(2-difluoromethoxyphenylmethanesulfanyl)-2(R)-[2,2,2-trifluoro-1(RS)-(4-fluorophenyl)ethylamino]propionic acid (153 mg, 0.338 mmol) in MeOH (10 mL) was added a solution of OXONE® (314 mg, 0.51 mmol) in water (10 mL) at room temperature. After stirring for 30 min, the methanol was removed and extracted with ethyl acetate (100 mL), then washed with brine and dried with $MgSO_4$. Removal of the solvent gave 3-(2-difluoromethoxy-phenylmethanesulfonyl)-2(R)-[2,2,2-trifluoro-1 (RS)-(4-fluorophenyl)-ethylamino]propionic acid (157 mg).

Step 5

To a solution of 3-(2-difluoromethoxyphenylmethanesulfonyl)-2(R)-[2,2,2-trifluoro-1(RS)-(4-fluorophenyl)ethylamino]propionic acid (157 mg, 0.325 mmol) in DMF (5 mL) was added 1-aminocyclopropanecarbonitrile hydrochloride (46.4 mg, 0.39 mmol), HATU (186.3 mg, 0.49 mmol) and DIPEA (63.2 mg, 0.49 mmol). After 1 h, the reaction mixture was extracted with ethyl acetate (100 mL) and washed with satured $NaHCO_3$ and brine. After drying with $MgSO_4$, the solvent was removed and the residue was purified by column chromatograph yield the title compound (125 mg).

HNMR ($CDCl_3$): 7.69(1H, s), 7.5-7(8H, m), 6.5 (1H, t, J=58.8 Hz), 4.47 (2H, dd), 4.25 (1H, dd), 3.65-3.6 (1H, m), 3.45-3.35 (1H, m), 3.3-3.1 (1H, m), 1.2-1.1 (2H, m), 1.01-0.9 (2H, m). LC-MS: 548(M−1), 550.1 (M+1), 572(M+Na).

Example 4

Synthesis of N-(4-cyano-1,1-dioxohexahydro-1$\lambda^6$-thiopyran-4-yl)-3-(2-difluoromethoxy-phenylmethanesulfonyl-2(R)-(2,2,2-trifluoro-1(S)-4-fluorophenylethylamino)propionamide (Method B)

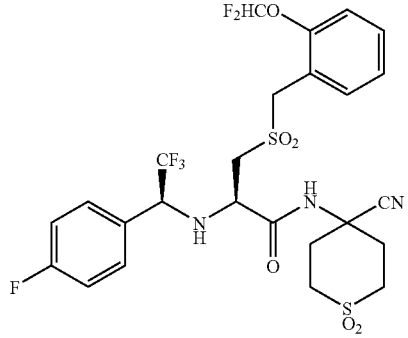

Proceeding as described in Example 6, Step 5 above, but substituting 1-aminocyclopropanecarbonitrile hydrochloride with 4-amino-4-cyanotetrahydrothiopyran provided N-(4-cyano-tetrahydrothiopyran-4-yl)-3-(2-difluoromethoxyphenylmethanesulfanyl)-2(R)-(2,2,2-trifluoro-1(RS)-4-fluorophenylethylamino)propionamide which was converted to N-(4-cyanotetrahydrothiopyran-4-yl)-3-(2-difluoromethoxyphenylmethanesulfonyl-2(R)-(2,2,2-trifluoro-1(RS)-4-fluorophenyl-ethylamino)propionamide as described in Example 3 above. The title compound was isolated via column chromatography.

HNMR (CDCl$_3$): 7.69(1H, s), 7.5-7(8H, m), 6.5 (1H, t, J=74 Hz), 4.6 (2H, dd), 4.2 (1H, d), 3.8 (1H, m), 3.5-2.8 (4H, m), 2.7-1.9 (3H, m), 1.8-1.4 (2H, m), 1.2-1.1 (2H, m). LC-MS: 640.2(M−1), 641.8 (M+1)

Example 5

Synthesis of N-(4-cyanotetrahydropyran-4-yl)-3-(2-difluoromethoxyphenylmethanesulfonyl-2(R)-(2,2,2-trifluoro-1(S)-4-fluorophenylethylamino)propionamide

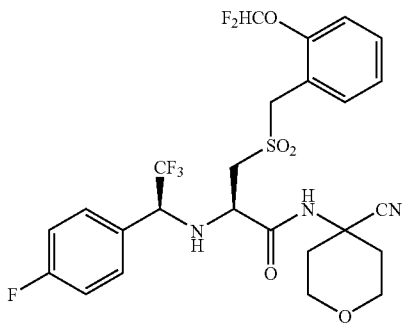

Proceeding as described in Example 6, Step 5 above, but substituting 1-aminocyclopropane-carbonitrile hydrochloride with 4-amino-4-cyanotetrahydropyran (prepared as described in PCT application publication No. WO 01/19816, page 141, Example 2) provided N-(4-cyanotetrahydropyran-4-yl)-3-(2-difluoromethoxyphenylmethanesulfanyl-2(R)-(2,2,2-trifluoro-1(RS)-4-fluorophenylethylamino)propionamide which was converted to N-(4-cyanotetrahydropyran-4-yl)-3-(2-difluoromethoxyphenylmethanesulfonyl-2(R)-(2,2,2-trifluoro-1 (RS)-4-fluorophenylethylamino)propionamide as described in Example 3 above. The title compound was isolated via column chromatography.

HNMR (CDCl$_3$): 7.69(1H, s), 7.5-7(8H, m), 6.6 (1H, t, J=73.6 Hz), 4.63 (2H, dd), 4.38 (1H, m), 4-3.2 (8H, m), 2.3-2.1 (2H, dd), 1.8-1.5 (2H, m). LC-MS: 592.2(M−1), 593.8 (M+1), 615.7 (M+Na).

Example 6

Synthesis of N-(1-cyanocyclopropyl)-3-(6-trifluoromethylpyridin-2-ylmethanesulfonyl)-2(R)-(2,2,2-trifluoro-1(S)-phenylethylamino)propionamide (Method B)

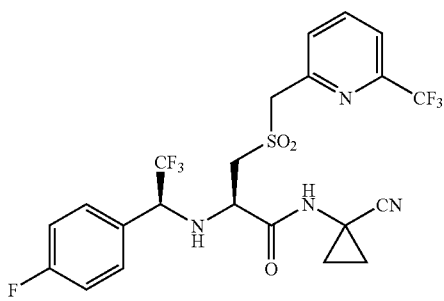

Step 1
6-Trifluoromethylpyridine-2-carboxylic acid was prepared as described in (Schlosser, M. and Marull, M. *Eur. J. Org. Chem.* 2003, 1569-1575.

Step 2
To a suspension of 6-trifluoromethylpyridine-2-carboxylic acid (2.53 g, 13.2 mmol) in THF (50 mL) cooled to −5° C. was added triethylamine (1.84 mL, 13.2 mmol) followed by addition of ethyl chloroformate (1.26 mL, 13.2 mmol) and the reaction mixture was stirred for 30 min at 0° C. Lithium borohydride (718 mg, 33 mmol) was added in portions, maintaining the temperature below −5° C. After the addition was complete, the reaction was allowed to warm to room temperature and stirred for 1 h. Temperature was lowered to −5° C. and methanol (10 mL) was added followed by addition of aqueous sodium hydroxide (10 mL, 10%). After the addition of ethyl acetate (50 mL) and water (40 mL), dilute hydrochloric acid was added to obtain pH=5.0. After washing aqueous layer thoroughly with ethyl acetate the combined organic extracts were dried over MgSO$_4$ and concentrated. Purification by flash column (30% EtOAc-Hexane) gave (6-trifluoromethylpyridin-2-yl)methanol (760 mg) as an oil.

Step 3
(6-Trifluoromethylpyridin-2-yl)methanol (760 mg, 4.3 mmol) was dissolved in CH$_2$Cl$_2$ and thionyl chloride was added slowly at room temperature. The reaction mixture was stirred at room temperature for 4 h. Solvent was removed under the reduced pressure, the pH was adjusted to 5, and the product was extracted with EtOAc. Purification by flash column (5% EtOAc-Hexane) gave 2-chloromethyl-6-trifluoromethylpyridine (200 mg) as a white solid.

Step 4
2(R)—N-tert-butoxycarbonylamino-3-(pyridin-2-ylmethylsulfanyl)propionic acid was prepared as described in Example 4, Step 1.

Step 5
2(R)-tert-Butoxycarbonylamino-3-(6-trifluoromethylpyridin-2-ylmethylsulfanyl)-propionic acid (760 mg, 2 mmol) was dissolved in DMF and 1-aminocyclopropanecarbonitrile hydrochloride (284 mg, 2.4 mmol), HATU (912 mg, 2.4 mmol) and N-methylmorpholine (0.9 mL, 81 mmol) were added. After stirring for 4 h at room temperature, saturated NaHCO$_3$ solution and ethyl acetate were added and stirring was continued for an additional 20 min. The reaction mixture was extracted with ethyl acetate and the combined organic layer was dried by MgSO$_4$, filtered, and concentrated under reduced pressure. Purification by flash column (100% CH$_2$Cl$_2$) gave [1-(1-cyano-cyclopropylcarbamoyl)-2(R)-(6-trifluoromethylpyridin-2-ylmethyl-sulfanyl)ethyl]carbamic acid tert-butyl ester (340 mg) as an oil.

Step 6
[1-(1-Cyanocyclopropylcarbamoyl)-2(R)-(6-trifluoromethylpyridin-2-ylmethylsulfanyl)-ethyl]-carbamic acid tert-butyl ester (340 mg) was dissolved in THF and 3 eq. of methanesulfonic acid was added. After stirring overnight, water (1 mL) was added and solid NaHCO$_3$ was added until no bubbles were observed. The reaction mixture was extracted with ethyl acetate. The organic layer was dried with MgSO$_4$, filtered and concentrated under the reduced pressure to get 2(R)-amino-N-(1-cyanocyclopropyl)-3-(6-trifluoromethylpyridin-2-ylmethylsulfanyl)propionamide as an oil.

Step 7
2(R)-Amino-N-(1-cyanocyclopropyl)-3-(6-trifluoromethylpyridin-2-ylmethylsulfanyl)-propionamide (86 mg, 0.25 mmol), NMM (0.054 mL, 0.5 mmol) and molecular sieves were added in THF. After 5 min, trifluoromethanesulfonic acid 2,2,2-trifluoro-1-(4-fluorophenyl)ethyl ester (122 mg, 0.37 mmol) was added at room temperature. The reaction mixture was stirred at room temperature overnight. Solvent was removed under the reduced pressure and N-(1-cyanocyclo-propyl)-2(R)-[2,2,2-trifluoro-1 (RS)-(4-fluorophenyl) ethylamino]-3-(6-trifluoromethylpyridin-2-ylmethyl-sulfanyl)propionamide was purified by flash column (30% EtOAc-Hexane) to get (40 mg) of pure product as an oil. LC-MS: 521 (M+1), 543 (M+23), 519 (M−1). This was converted to N-(1-cyanocyclopropyl)-2(R)-[2,2,2-trifluoro-1(RS)-(4-fluorophenyl)ethylamino]-3-(6-trifluoromethylpyridin-2-ylmethyl-sulfonyl)propionamide compound as described in Example 3 above. Two diastereomers are separated by flash column (1% MeOH—$CH_2Cl_2$) to give the title compound.

NMR (DMSO-$d_6$): 0.74 (1H, m), 0.97 (1H, m), 1.33 (2H, m), 3.27 (1H, m), 3.45 (2H, m), 3.72 (1H, m), 4.39 (1H, m), 4.93 (2H, m), 7.19 (2H, t), 7.42 (2H, m), 7.77 (1H, d), 7.92 (1H, d), 8.15 (1H, t), 9.01 (1H, s). LC-MS: 553(M+1), 575 (M+23), 551 (M−1).

Example 7

N-(1-cyanocyclopropyl)-3-cyclopropylmethanesulfonyl-2(R)-(2,2,2-trifluoro-1 (S)-4-fluorophenylethylamino)propionamide

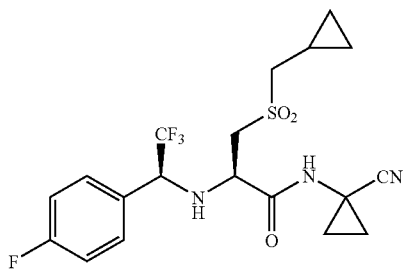

Step 1

To a slurry of S-trityl-L-cysteine (4.86 g, 13.37 mmol) in dichloromethane (97 mL, 20 mL/g AA) at room temperature was added diisopropylethylamine (9.32 mL, 53.48 mmol) followed by a solution of trifluoromethanesulfonic acid 2,2,2-trifluoro-1(RS)-phenylethyl ester (5.32 g, 16.04 mmol) (major enantiomer (S), 90 ee) in dichloromethane (15 mL) via syringe all at once. After 19 h, the reaction mixture was concentrated on the rotovap to give an oil. Diethyl ether was added and the solution was washed with 1N HCl and brine. The organic layer was dried over $MgSO_4$, filtered, and concentrated. Flash chromatography of the residue with 2 hexanes/1 ethyl acetate/0.25% acetic acid as the eluent provided 2(R)-[2,2,2-trifluoro-1(RS)-(4-fluorophenyl)ethylamino]-3-tritylsulfanyl-propionic acid (6 g) (major diastereomer (R,S), 90 de) as an oil/foam.

Step 2

Into a stirred solution of 2(R)-[2,2,2-trifluoro-1(RS)-(4-fluorophenyl)ethylamino]-3-tritylsulfanylpropionic acid (1.93 g, 3.58 mmol) in dichloromethane (5 mL) was added trifluoroacetic acid (489 mg, 4.29 mmol) and triethylsilane (498.9 mg, 4.29 mmol) at room temperature. After 16 h, the reaction was completed and the solvent was removed under vacuum. The residue was dissolved in 1N NaOH solution (15 mL) and extracted with hexane to remove the by products. To the aqueous solution, was added cyclopropylmethane bromide (482.9 mL, 3.58 mmol) in dioxane (15 mL) at room temperature. After 16 h, the organic solvent was removed under vacuum and the aqueous layer was acidified with 1N HCl, then extracted with ethyl ether (150 mL). The organic layer was washed with brine, dried with $MgSO_4$, and concentrated to give 2(R)-[2,2,2-trifluoro-1(RS)-(4-fluorophenyl) ethylamino]-3-cyclopropylmethanesulfanylpropionic acid (1.32 g).

Step 3

To a solution of 2(R)-[2,2,2-trifluoro-1(RS)-(4-fluorophenyl)ethylamino]-3-cyclopropyl-methanesulfanylpropionic acid (1.32 g) in DMF (10 mL) was added 1-aminocyclopropane-carbonitrile HCl salt (428.4 mg, 3.6 mg), HATU (1.64 g, 4.32 mmol), and DIPEA (1.39 g, 10.8 mmol) at room temperature. After 2 h, the reaction mixture was diluted with ethyl ether (150 mL) and washed with saturated $NaHCO_3$ and brine, dried over $MgSO_4$, and concentrated to provide N-(1-cyanocyclopropyl)-3-cyclopropyl-methanesulfanyl-2(R)-(2,2,2-trifluoro-1(RS)-4-fluorophenyl-ethylamino)propionamide (1.03 g). LC-MS: 414.1(M-1), 416.2 (M+1), 438.1 (M+Na).

Step 4

To a solution of N-(1-cyanocyclopropyl)-3-cyclopropylmethanesulfanyl-2(R)-(2,2,2-trifluoro-1(RS)-4-fluorophenylethylamino)propionamide (1.03 g) in MeOH (10 mL) was added a solution of OXONE® (2.29 g, 3.72 mmol) in water (10 mL) at room temperature. After 2 h, the organics were removed under vacumn and the product was extracted into ethyl acetate (150 mL). The combined organic extracts were washed with brine, dried over $MgSO_4$, and concentrated to yield a white solid product (1.1 g). The solid was crystallized from a hot mixture of ethyl acetate (10 mL) and hexane (10 mL), to yield the title compound (622 mg) as a white crystalline product.

H-NMR ($CDCl_3$): δ 8.56(1H, s, NH), 8.35-8.25 (2H, m), 8.1-8(2H, m), 5.26 (1H, ab), 4.65-4.55 (1H, m), 4.46 (1H, ab), 4.25 (1H, ab), 4(2H, d), 2.48-2.4 (3H, m), 2.12-2(3H, m), 1.7-1.6 (2H, m), 1.4-1.3 (2H, m). LC-MS: 446(M−1), 448 (M+1), 470.3 (M+Na).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:

1. A process of preparing a compound of Formula (I):

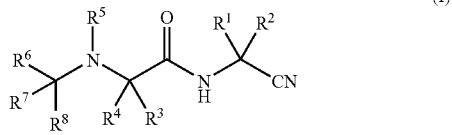

wherein:

$R^1$ is hydrogen or alkyl;

$R^2$ is hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, or -alkylene-X—$R^9$ (where X is —O—, —$NR^{10}$—, —$CONR^{11}$—, —$S(O)_{n1}$—, —$NR^{12}CO$—, —CO—, or —C(O)O— where n1 is 0-2, and $R^9$, $R^{10}$, $R^{11}$, and $R^{12}$ are independently hydrogen, alkyl, haloalkyl, cycloalkyl, cycloalkylalkyl, aryl, aralkyl, heteroaryl, or heteroaralkyl) wherein the aromatic or alicyclic ring in $R^2$ is optionally substituted with one, two, or three $R^a$ independently selected from alkyl, haloalkyl, alkoxy, hydroxy, haloalkoxy, halo, carboxy, alkoxycarbonyl, amino, monosubstituted amino, disubstituted amino, nitro, aryloxy, benzyloxy, acyl, or arylsulfonyl and further where the aromatic or alicyclic ring in $R^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or $R^1$ and $R^2$ taken together with the carbon atom to which both $R^1$ and $R^2$ are attached form (i) cycloalkylene optionally substituted with one or two $R^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl or (ii) heterocyclylalkylene optionally substituted with one to four $R^c$ which are independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —$S(O)_{n2}R^{14}$, -alkylene-$S(O)_{n2}$—$R^{15}$, —$COOR^{16}$, -alkylene-$COOR^{17}$, —$CONR^{18}R^{19}$, or -alkylene-$CONR^{20}R^{21}$ (where n2 is 0-2 and $R^{14}$-$R^{17}$, $R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl) wherein the aromatic or alicyclic ring in the groups attached to cycloalkylene or heterocyclylalkylene is optionally substituted with one, two, or three substituents independently selected from alkyl, haloalkyl, alkoxy, hydroxy, haloalkoxy, halo, carboxy, alkoxycarbonyl, amino, monosubstituted amino, disubstituted amino, or acyl;

$R^3$ is hydrogen or alkyl;

$R^4$ is alkyl, haloalkyl, cycloalkylalkyl, aryl, aralkyl, heteroaryl, heteroaralkyl, heterocyclylalkyl, or -alkylene-$X^1$—$R^{22}$ wherein $X^1$ is —$NR^{23}$—, —O—, —$S(O)_{n3}$—, —CO—, —COO—, —OCO—, —$NR^{23}CO$—, —$CONR^{23}$—, —$NR^{23}SO_2$—, —$SO_2NR^{23}$—, —$NR^{23}COO$—, —$OCONR^{23}$—, —$NR^{23}CONR^{24}$—, or —$NR^{23}SO_2NR^{24}$— (where $R^{23}$ and $R^{24}$ are independently hydrogen, alkyl, or acyl and n3 is 0-2) and $R^{22}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl wherein said alkylene chain in -alkylene-$X^1$—$R^{22}$ is optionally substituted with one to six halo and wherein the aromatic or alicyclic ring in $R^4$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl; or $R^3$ and $R^4$ together with the carbon atom to which they are attached form cycloalkylene;

$R^5$ is hydrogen or alkyl;

$R^6$ is cycloalkyl, aryl, aralkyl, heteroaryl, heteroaralkyl, or heterocyclyl wherein the aromatic or alicyclic rings in $R^6$ are optionally substituted by one, two, or three $R^e$ independently selected from alkyl, halo, hydroxy, alkoxy, haloalkyl, haloalkoxy, oxo, cyano, nitro, acyl, aryl, aralkyl, heteroaryl, heteroaralkyl, heterocyclyl, cycloalkyl, cycloalkylalkyl, carboxy, alkoxycarbonyl, —$B(OH)_2$, or 4,4,5,5-tetramethyl-[1,3,2]dioxaborolan-2-yl and further where the aromatic or alicyclic rings in $R^e$ is optionally substituted by one, two or three $R^f$ independently selected from alkyl, alkoxy, haloalkyl, alkylthio, alkylsulfonyl, aminosulfonyl, haloalkoxy, halo, hydroxy, carboxy, cyano, nitro, aryl or cycloalkyl;

$R^7$ is haloalkyl; and $R^8$ is hydrogen, alkyl, or haloalkyl; or a pharmaceutically acceptable salt thereof, which process comprises:

(A)

(1) reacting a compound of formula (a):

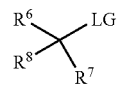

where $R^6$, $R^7$, and $R^8$ are as defined for the compound of Formula (I) above and LG is a leaving group, with a compound of formula (b):

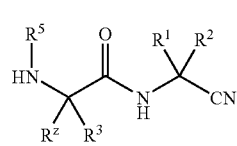

where $R^1$, $R^2$, $R^3$ and $R^5$ are as defined for the compound of Formula (I) above and $R^z$ is $R^4$ or -alkylene-$X^1$—Z where $X^1$ and $R^4$ are as defined for the compound of Formula (I) above and Z is a protecting group; to provide a compound of Formula (I) when $R^z$ is $R^4$; or a compound of formula (Ia):

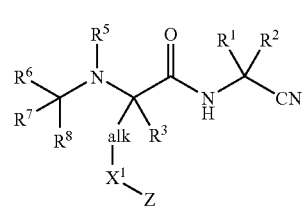

where $R^1$, $R^2$, $R^3$, $R^5$-$R^8$, $X^1$, and Z are as defined above;

(i) optionally modifying any of the $R^1$, $R^2$, $R^3$, and $R^5$-$R^8$ group(s) in the compound of formula (Ia);

(ii) removing the Z group in the compound of formula (Ia) obtained in Step (i) above, to give the corresponding compound of Formula (I) where $R^4$ is -alkylene-$X^1$H;

(iii) converting the compound obtained in Step (ii) above, to a compound of Formula (I) where $R^4$ is -alkylene-$X^1$—$R^{22}$ where $R^{22}$ is as defined for the compound of Formula (I) above except $R^{22}$ is other than hydrogen;

(iv) optionally modifying any of the $R^1$-$R^8$ group(s) in a compound of Formula (I) to provide a corresponding compound of Formula (I);

(v) optionally forming an acid addition salt of a compound of Formula (I); or (vi) optionally forming a free base of a compound of Formula (I); or (2) reacting a compound of formula (a) with a compound of formula (b'):

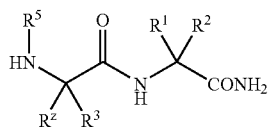

where $R^1$, $R^2$, $R^3$ and $R^5$ are as defined for the compound of Formula (I) above and $R^z$ is $R^4$ or -alkylene-$X^1$—Z where $X^1$ and $R^4$ are as defined for the compound of Formula (I) above and Z is a protecting group; to provide a compound of formula (Ib) or (Ic):

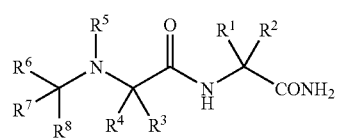

where $R^1$-$R^8$ are as defined for compound of Formula (I) above;
or

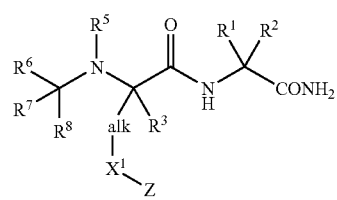

where $R^1$, $R^2$, $R^3$, $R^5$-$R^8$, $X^1$, and Z are as defined above;

(i) optionally modifying any of the $R^1$-$R^8$ group(s) in the compound of formula (Ib) or (Ic) to provide a corresponding compound of formula (Ib) or (Ic);

(ii) optionally removing the Z group from the compound of formula (Ic) to give a compound of Formula (Ib) where $R^4$ is -alkylene-$X^1$H;

(iii) optionally converting the compound obtained in Step (ii) above, to a compound of formula (Ib) where $R^4$ is -alkylene-$X^1$—$R^{22}$ where $R^{22}$ is as defined for the compound of Formula (I) above except $R^{22}$ is other than hydrogen;

(iv) converting the —$CONH_2$ group to —CN group in the compound (Ib) and (Ic) to provide a compound of Formula (I) and formula (Ia) respectively;

(v) optionally modifying any of the $R^1$, $R^2$, $R^3$, $R^4$, and $R^5$-$R^8$ group(s) in compound of formula (Ia);

(vi) removing the Z group from compound of formula (Ia) obtained in Step (iv) or (v) above, to give a compound of Formula (I) where $R^4$ is -alkylene-$X^1$H;

(vii) converting the compound obtained in Step (vi) above, to a compound of Formula (I) where $R^4$ is -alkylene-$X^1$—$R^{22}$ where $R^{22}$ is as defined for the compound of Formula (I) above except $R^{22}$ is other than hydrogen;

(viii) optionally modifying any of the $R^1$-$R^8$ group(s) in a compound of Formula (I) to provide a corresponding compound of Formula (I);

(ix) optionally forming an acid addition salt of a compound of Formula (I); or (x) optionally forming a free base of a compound of Formula (I); or (B)

(1) reacting a compound of formula (a):

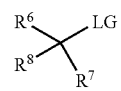

where $R^6$, $R^7$, and $R^8$ are as defined for the compound of Formula (I) above, with an amino acid of formula (c):

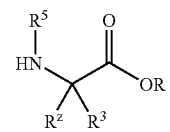

where:
R is hydrogen or a carboxy protecting group;
$R^3$ and $R^5$ are as defined for the compound of Formula (I) above; and
$R^z$ is $R^4$ or -alkylene-$X^1$—Z where $X^1$ and $R^4$ are as defined for the compound of Formula (I) above and Z is a protecting group; to provide a compound of formula (d):

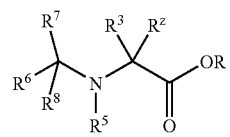

where R, $R^3$, $R^z$, $R^5$, $R^6$, $R^7$, and $R^8$ are as defined above;

(i) optionally modifying any of the $R^4$, $R^5$, $R^6$, $R^7$, and $R^8$ group(s) in the compound (d) obtained in Step (1) above;

(ii) optionally removing the Z group from compound (d) when $R^z$ is -alkylene-$X^1$—Z in the compound obtained in Step (1) or (i) above, to give a compound of formula (d) where $R^z$ is $R^4$ where $R^4$ is -alkylene-$X^1$H;

(iii) optionally converting the compound obtained in Step (ii) above, to a compound of formula (d) where $R^z$ is $R^4$ where $R^4$ is -alkylene-$X^1$—$R^{22}$ where $R^{22}$ is as defined for the compound of Formula (I) above except $R^{22}$ is other than hydrogen;

(iv) optionally modifying any of the $R^4$, $R^5$, $R^6$, $R^7$, and $R^8$ group(s) in the compound obtained from Step (iii) above;

(v) deprotecting the carboxy group in the compound obtained from Step (1), (i), (iii), or (iv) above, where R is a carboxy protecting group to provide the corresponding compound of formula (d) where R is hydrogen;

(vi) converting the acid obtained in Step (1), (i), (ii), (iii), (iv), or (v) above, where R is hydrogen to an activated acid derivative;

(vii) reacting the activated acid derivative from Step (vi) above, with a compound of formula (e) or as salt thereof:

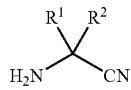
(e)

where $R^1$ and $R^2$ are as defined for the compound of Formula (I) above to provide a compound of Formula (I) when $R^z$ is $R^4$; or a compound of formula (Ia):

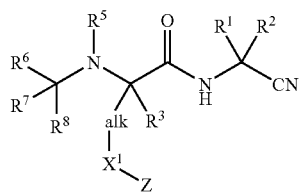
(Ia)

(viii) optionally modifying any of the $R^1$, $R^2$, $R^3$, $R^4$, and $R^6$-$R^8$ group(s) in compound of formula (Ia);

(ix) removing the Z group from compound of formula (Ia) obtained in Step (vii) or (viii) above, to give the corresponding compound of Formula (I) where $R^4$ is -alkylene-$X^1$H;

(x) converting the compound obtained in Step (ix) above, to a compound of Formula (I) where $R^4$ is -alkylene-$X^1$—$R^{22}$ where $R^{22}$ is as defined for the compound of Formula (I) above except $R^{22}$ is other than hydrogen;

(xi) optionally modifying any of the $R^1$-$R^8$ group(s) in a compound of Formula (I) to provide the corresponding compound of Formula (I);

(xii) optionally forming an acid addition salt of a compound of Formula (I); or (xiii) optionally forming a free base of a compound of Formula (I); or (2) reacting the activated acid derivative from Step (vi) above, with a compound of formula (e') or as salt thereof:

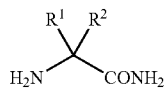
(e')

where $R^1$ and $R^2$ are as defined for the compound of Formula (I) above to provide a compound of formula (Ib) or (Ic):

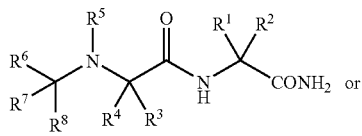
(Ib)

-continued

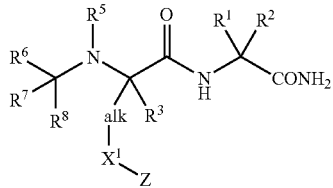
(Ic)

(i) optionally modifying any of the $R^1$-$R^8$ group(s) in a compound of formula (Ib) or (Ic) to provide a corresponding compound of formula (Ib) or (Ic);

(ii) optionally removing the Z group from compound of formula (Ic) to give the corresponding compound of formula (Ib) where $R^4$ is -alkylene-$X^1$H;

(iii) optionally converting the compound obtained in Step (ii) above, to a compound of formula (Ib) where $R^4$ is -alkylene-$X^1$—$R^{22}$ where $R^{22}$ is as defined for the compound of Formula (I) above except $R^{22}$ is other than hydrogen;

(iv) converting the —$CONH_2$ group to —CN group in the compound (Ib) and (Ic) to provide a compound of Formula (I) or formula (Ia);

(v) optionally modifying any of the $R^1$, $R^2$, $R^3$, $R^4$, and $R^6$-$R^8$ group(s) in a compound of formula (Ia);

(vi) removing the Z group in the compound of formula (Ia) obtained in Step (iv) or (v) above, to give a compound of Formula (I) where $R^4$ is -alkylene-$X^1$H;

(vii) converting the compound obtained in Step (vi) above, to a compound of Formula (I) where $R^4$ is -alkylene-$X^1$—$R^{22}$ where $R^{22}$ is as defined for the compound of Formula (I) above except $R^{22}$ is other than hydrogen;

(viii) optionally modifying any of the $R^1$-$R^8$ group(s) in a compound of Formula (I) to provide the corresponding compound of Formula (I);

(ix) optionally forming an acid addition salt of a compound of Formula (I); or (x) optionally forming a free base of a compound of Formula (I); or (C)

(1) reacting a compound of formula (a):

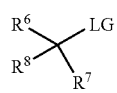
(a)

where $R^6$, $R^7$, and $R^8$ are as defined for a compound of Formula (I) above, with an amino alcohol of formula (f):

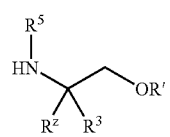
(f)

where:
R' is hydrogen or a hydroxy protecting group;
$R^3$ and $R^5$ are as defined for the compound of Formula (I) above;

$R^z$ is as defined for the compound of formula (c) above; to provide a compound of formula (g):

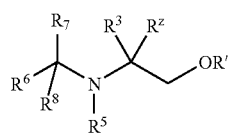

(g)

where R, $R^3$, $R^z$, $R^5$, $R^6$, $R^7$, and $R^8$ are as defined above;

(i) optionally modifying any of the $R^4$, $R^5$, $R^6$, $R^7$, and $R^8$ group(s) in the compound (g) obtained from Step (1) above;

(ii) removing the Z group in compound (g) when $R^z$ is -alkylene-$X^1$—Z obtained in Step (1) or (i) above, to give a compound of formula (g) where $R^z$ is $R^4$ where $R^4$ is -alkylene-$X^1$H;

(iii) converting the compound obtained in Step (ii) above, to a compound of formula (g) where $R^z$ is $R^4$ where $R^4$ is -alkylene-$X^1$—$R^{22}$ where $R^{22}$ is as defined for the compound of Formula (I) above except $R^{22}$ is other than hydrogen;

(iv) optionally modifying any of the $R^4$, $R^5$, $R^6$, $R^7$, and $R^8$ group(s) in the compound obtained from Step (iii) above;

(v) deprotecting the hydroxy group in the compound obtained from Step (1), (i), (iii), or (iv) above, where R' is a hydroxy protecting group and $R^z$ is $R^4$ to give a compound of formula (g) where R' is hydrogen;

(vi) converting the compound obtained in Step (1), (i), (ii), (iii), (iv), or (v) above, where R' is hydrogen to a compound of formula (h):

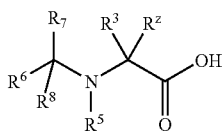

(h)

where $R^z$ is $R^4$ as defined in Formula (I) above and $R^3$, $R^5$, $R^6$, $R^7$, and $R^8$ are as defined in Formula (I) above using an oxidizing reagent;

(vii) converting compound obtained from Step (vi) above, to an activated acid derivative;

(viii) reacting activated acid derivative with a compound of formula (e) or a salt thereof:

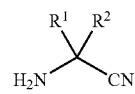

(e)

where $R^1$ and $R^2$ are as defined for Formula (I) above to provide a compound of Formula (I);

(ix) optionally modifying any of the $R^1$-$R^8$ groups to provide a corresponding compound of Formula (I);

(x) optionally forming an acid addition salt of a compound of Formula (I); and (xi) optionally forming a free base of a compound of Formula (I); or (2) reacting the activated acid derivative from Step (vii) above, with a compound of formula (e') or a salt thereof:

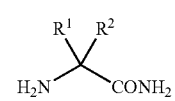

(e')

where $R^1$ and $R^2$ are as defined for the compound of Formula (I) above to provide a compound of formula (Ib):

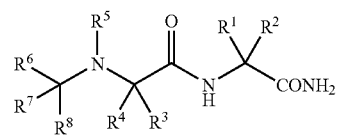

(Ib)

(i) optionally modifying any of the $R^1$-$R^8$ group(s) to provide a corresponding compound of formula (I');

(ii) converting the —$CONH_2$ group to —CN group in the compound from Step (i) above to provide a compound of Formula (I);

(iii) optionally modifying any of the $R^1$-$R^8$ group(s) to provide a corresponding compound of Formula (I);

(iv) optionally forming an acid addition salt of a compound of Formula (I); or (v) optionally forming a free base of a compound of Formula (I);

provided that LG is not bromo, mesylate, tosylate, p-nitrophenylsulfonate or 2,4-dinitrophenylsulfonate.

* * * * *